United States Patent [19]

Strupczewski et al.

[11] Patent Number: 4,469,869

[45] Date of Patent: Sep. 4, 1984

[54] 3-(4-PIPERIDINIUM)-1,2-BENZISOXAZOLES

[75] Inventors: Joseph T. Strupczewski, Flemington, N.J.; Beth A. Gardner, San Jose, Calif.; Richard C. Allen, Flemington, N.J.

[73] Assignee: Hoechst-Roussel Pharmaceuticals, Inc., Somerville, N.J.

[21] Appl. No.: 492,846

[22] Filed: May 9, 1983

Related U.S. Application Data

[62] Division of Ser. No. 407,235, Aug. 11, 1982, Pat. No. 4,408,054, which is a division of Ser. No. 319,871, Nov. 12, 1981, Pat. No. 4,355,037.

[51] Int. Cl.$^3$ .......................................... C07D 413/04
[52] U.S. Cl. .................................................. 546/198
[58] Field of Search ........................................ 546/198

[56] References Cited

U.S. PATENT DOCUMENTS 4,352,811 10/1982 Strupczewski et al. ........ 546/198 X

*Primary Examiner*—Richard A. Schwartz
*Attorney, Agent, or Firm*—Raymond R. Wittekind

[57] ABSTRACT

Novel 3-(4-piperidyl)-1,2-benzisoxazoles, intermediates and processes for the preparation thereof, and methods for alleviating pain utilizing compounds or compositions thereof are disclosed.

2 Claims, No Drawings

3-(4-PIPERIDINIUM)-1,2-BENZISOXAZOLES

This is a division of application Ser. No. 407,235 filed Aug. 11, 1982, now U.S. Pat. No. 4,408,054, which is a division of application Ser. No. 319,871, filed Nov. 12, 1981, now U.S. Pat. No. 4,355,037.

The present invention relates to novel 3-(4-piperidyl)-1,2-benzisoxazoles. More particularly, the present invention relates to 3-(4-piperidyl)-1,2-benzisoxazoles of formula 1

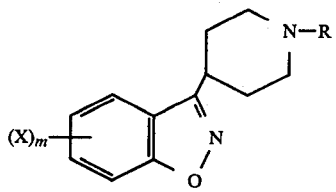

wherein R is hydrogen, loweralkyl, loweralkenyl, cycloalkylloweralkyl, phenylloweralkyl, hydroxy, diloweralkylaminoloweralkyl, cyano, cyanomethyl,

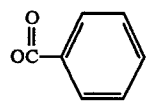

or a group of the formula

wherein $R^1$ is hydrogen, loweralkyl or a group of the formula $OR^2$ wherein $R^2$ is phenyl or benzyl; X is hydrogen, loweralkyl, loweralkoxy, halogen or hydroxy; m is 1 or 2; the geometrical isomers and optical antipodes thereof; or the pharmaceutically acceptable acid addition thereof, which are useful as analgetic agents, alone or in combination with inert pain-alleviating adjuvants.

Preferred 3-(4-piperidyl)-1,2-benzisoxazoles of the present invention are those compounds wherein R is hydrogen, lowerlalkyl, loweralkenyl or cycloalkylloweralkyl. Most preferred 3-(4-piperidyl)-1,2-benzisoxazoles of the present invention are those compounds wherein R is loweralkenyl or cycloalkylloweralkyl.

Subgeneric to 3-(4-piperidyl)-1,2-benzisoxazoles of the present invention are compounds wherein:
(a) R is phenylloweralkyl;
(b) R is hydroxy or

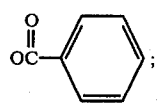

(c) R is diloweralkylaminoalkyl;
(d) R is cyano or cyanomethyl; and
(e) R is a group of the formula

wherein $R^1$ is hydrogen, loweralkyl or a group of the formula $OR^2$ wherein $R^2$ is phenyl or benzyl.

The present invention also relates to benzoylpiperidines of formula 2

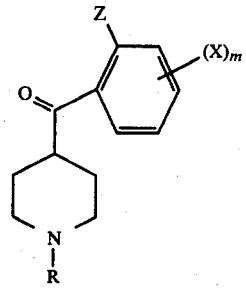

wherein R is hydrogen, loweralkyl, benzyl or a group of the formula

wherein $R^1$ is hydrogen, loweralkyl or a group of the formula $OR^2$ wherein $R^2$ is benzyl; X is hydrogen, loweralkyl, loweralkoxy, halogen or hydroxy; Z is halogen or hydroxy; m is 1 or 2; the optical antipodes thereof; or salts thereof when R is hydrogen, loweralkyl or benzyl, and to benzoylpiperidine oximes and O-derivatives thereof of formula 3

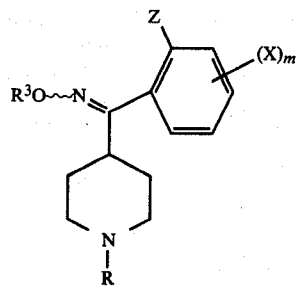

wherein R is hydrogen, loweralkyl, loweralkenyl or a group of the formula

wherein $R^1$ is hydrogen, loweralkyl or a group of the formula $OR^2$ wherein $R^2$ is benzyl; $R^3$ is hydrogen or a group of the formula

wherein $R^4$ is hydrogen or loweralkyl; X is hydrogen, loweralkoxy, loweralkyl halogen or hydroxy; Z is halogen or hydroxy; m is 1 or 2; the geometric isomers and optical antipodes thereof; or salts thereof when R is hydrogen, loweralkyl, or loweralkenyl; useful as intermediates for the preparation of the hereinbefore mentioned 3-(4-piperidyl)-1,2-benzisoxazoles.

As used through the specification and appended claims, the term "alkyl" refers to a straight or branched chain hydrocarbon radical containing no unsaturation and having 1 to 10 carbon atoms such as methyl, ethyl, 1-propyl, 2-propyl, 1-butyl, 1-pentyl, 2-pentyl, 3-hexyl, 4-heptyl, 2-octyl, 3-nonyl, 4-decyl and the like; the term "alkenyl" refers to a straight or branched chain hydrocarbon radical containing unsaturation in the form of a single carbon to carbon double bond and having from 3 to 10 carbon atoms such as propenyl, 2-butenyl, 2-methyl-2-butenyl, 3-hexenyl, 3-ethyl-2-pentenyl, 3-methyl-3-heptenyl, nonenyl, decenyl, and the like; the term "cycloalkyl" refers to a saturated hydrocarbon group possessing at least one carbocyclic ring, the ring containing from 3 to 10 carbon atoms such as cyclopropyl, cyclobutyl, cyclopentyl, cyclohexyl, cycloheptyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, 2-methyloctoxy, octoxy, decoxy and the like; the term "alkanol" refers to a compound formed by a combination of an alkyl group and hydroxy radical. Examples of alkanols are methanol, ethanol, 1- and 2-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like; the term "halogen" refers to a member of the family fluorine, chlorine, bromine or iodine. The term "alkanoyl" refers to the radical formed by removal of the hydroxyl function from an alkanoic acid. Examples of alkanoyl groups are formyl, acetyl, propionyl, 2,2-dimethylacetykl, hexanoyl, octanoyl, decanoyl and the like. The term "lower" as applied to any of the aforementioned groups refers to a group having a carbon skeleton containing up to and including 7 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diasteromeric salts of those instant compounds characterized by the presence of a basic amino group and an optically active acid, or by the synthesis from optically active precursors.

The benzoylpiperidine oximes and O-derivatives of formula 3 thereof exist in isomeric Z- and E-forms. For example, 1-acetyl-4-(4,5-dimethoxy-2-hydroxy)piperidine oxime exists in the Z- and E-isomeric forms, 4 and 5, respectively, as shown below:

the hydroxyl group of the oxime function and the dimethoxyphenol moiety, are trans to each other. The wiggly (∿) line in the formulas of the oximes and O-derivatives thereof of formula 3 indicate that the compound may be the E- or Z-isomer. See B. Unterhalt, Method Chim. 6, 403 (1975), for a discussion of the E-Z nomenclature.

The present invention comprehends all optical isomers and racemic forms thereof and all geometric isomers of the compounds disclosed and claimed herein. The formulas of the compounds shown herein are intended to encompass all possible geometric and optical isomers of the compounds so depicted.

The novel 3-(4-piperdyl)-1,2-benzisoxazoles 1 of the present invention are synthesized by the processes illustrated in Reaction Schemes A to E.

To prepare the parent system, namely the 3-(4-piperidyl)-1,2-benzisoxazole system, the amino function of commercially available isonipecotic acid (hexahydropyridine-4-carboxylic acid) is protected by acylation to an N-alkanoyl derivative 8 which is condensed with an alkoxy- or halobenzene 10 to form a 4-benzoyl-piperidine 11 via a carboxylic acid halide 9. A 4-benzoylpiperidine 11, so obtained, is subsequently cyclized to a 3-(1-alkanoyl-4-piperidyl)-1,2-benzisoxazole 17 which is hydrolyzed to a 3-(1-unsubstituted-4-piperidyl)-1,2-benzisoxazole, 18. See Schemes A and B.

The 3-(4-piperidyl)-1,2-benzisoxazole system having an alkyl group at the 1-position of the piperidyl ring is prepared by condensing a 4-chloro-N-alkylpiperidine 19 with a benzonitrile 20 and cyclizing the 4-benzoyl-N-alkylpiperidine 21, so obtained, to a 3-(1-alkyl-4-piperidyl)-1,2-benzisoxazole 18. See Scheme C.

The acylation of isonepecotic acid 6 to its N-alkanoyl derivative 8 is performed by treating the secondary amine 6 with an anhydride 7 by methods well-known in the art. For example, treatment of isonepecotic acid 6 with acetic anhydride, in the presence or absence of a co-solvent such as acetic acid, at ambient temperature yields 8 where $R^5$ is methyl. To prepare the N-formyl derivative 8, wherein $R^5$ is hydrogen, acetic-formic acid anhydride, prepared from acetic anhydride and formic acid, is employed. In this case, it is preferable to utilize the mixed anhydride, acetic-formic acid anhydride, in situ and a slightly reduced temperature within the range of about 0° to about 25° C.

The conversion of a piperidine-4-carboxylic acid 8 to a piperidine-4-carboxylic acid halide 9 is also performed by conventional methods. For example, N-acetylisonipecotic acid (8, $R^5$ is methyl) is treated with thionyl chloride or thionyl bromide, in the presence or absence of a halocarbon solvent such as dichloromethane, chloroform, dichloroethane and the like, or a mixture thereof, at a temperature within the range of about

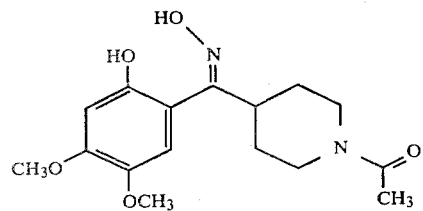

4

Z-isomer

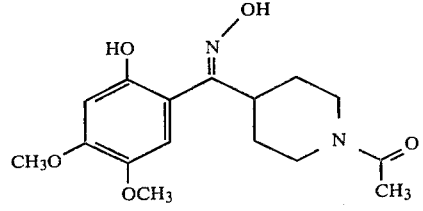

5

E-isomer

In the Z-isomer, the hydroxyl group of the oxime function and the dimethoxyphenol moiety, the group of greater priority, are cis to each other and in E-isomer, ambient temperature to about 75° C. Thionyl chloride is the preferred reagent. Dichloroethane and 65° C. are the preferred solvent and reaction temperature, respectively. For the preparation of the carboxylic acid chloride of N-formylisonipecotic acid, catalytic amounts of acetic anhydride may be employed.

The condensation of a piperidine-4-carboxylic acid halide 9 with an alkoxyl- or halobenzene 10 is accomplished by treating a slurry of the acid halide 9 and benzene derivative 10 with a Friedel-Crafts catalyst at about ambient temperature and heating the mixture to a temperature of about 50° to 150° C. to promote the reaction. Friedel-Crafts catalysts include aluminum chloride, ferric chloride, stannic chloride and the like. Aluminum chloride is preferred. The reaction temperature is not narrowly constant. However, a temperature of about 70° to 120° C. is preferred.

The condensation of a piperidine carboxylic acid 8 with an alkoxy- or halobenzene 10 is also accomplished by preparing a carboxylic acid halide 9 as hereinbefore described and, without isolation of the halide 9, treating the reaction mixture with the benzene component 10 and a Friedel-Crafts catalyst such as aluminum chloride, ferric chloride, stannic chloride and the like, at ambient temperature, and heating the reaction system at the reflux temperature thereof. Aluminum chloride is also the preferred Friedel-Crafts catalyst in the direct process.

The cyclization of a 1-alkanoyl-4-benzoylpiperidine 11, wherein Z is hydroxyl, to a 3-(1-alkanoyl-4-piperidyl)-1,2-benzisoxazole 17 is effected by first converting the benzoylpiperidine 11 to its oxime derivative 15, O-acylating the oxime derivative 15, and finally treating the O-alkanoylamine 16, so obtained, with a base.

The formation of an oxime 15 and its conversion to an 9-alkanoyl derivative 16 proceeds readily by methods well-known in the art. For example, treatment of a benzoylpiperidine 11 with hydroxylamine hydrochloride and ammonium acetate as an acid scavenger in an aqueous-alkanol such as aqueous ethanol at about the reflux temperature of the reaction mixture affords oxime 15, which is O-acylated by means of anhydrides such as formic anhydride, acetic anhydride and the like, or mixed anhydrides such as formic-acetic acid anhydride and the like, at reduced temperatures of about 0° C. to slightly elevated temperatures of about 75° C. in the presence or absence of a co-solvent. When a co-solvent, for example, a halocarbon such as dichloromethane, is employed, it is preferred to conduct the acylation at about ambient temperature. In the absence of a co-solvent, it is preferred to perform the reaction at about 60° C. When a mixed anhydride such as acetic-formic acid anhydride is used as the acylating agent, it is preferred to carry out the reaction in the absence of a co-solvent at a slightly reduced temperature within the range of about 0° to 20° C.

The elaboration of a 1,2-benzisoxazole 17 from an O-acyloxime 16 proceeds conveniently in the presence of a base, as hereinbefore indicated. Suitable bases include alkali and alkaline earth carbonates and bicarbonates such as potassium and magnesium carbonates, and sodium and calcium bicarbonates, and alkali and alkaline earth hydrides such as lithium, sodium, potassium or calcium hydrides. A solvent is employed to faciliate the cyclization. Among suitable solvents, there may be mentioned alkanols, i.e., methanol, ethanol, 2-propanol and the like, and polar aprotic substances such as dimethylacetamide, dimethylformamide and hexamethylphosphoramide, alone or admixed with an ethereal co-solvent such as diethylether, dimethoxyethane, dioxane or tetrahydrofuran. Generally, an alkanol is used as the solvent, when an alkali or alkaline earth carbonate or bicarbonate is employed as the base, and an aprotic polar substance is used as the solvent when an alkali or alkaline earth hydride is utilized as the base. Potassium carbonate in methanol and sodium hydride in dimethylformamide are the preferred cyclization reagents.

The temperature of the cyclization reaction is not critical. Usually, however, it is preferred to carry out the cyclization at the reflux temperature of the reaction mixture when an alkali or alkaline earth carbonate or bicarbonate is used, and at about ambient temperature to about 90° C., when an alkali or alkaline earth hydride is employed. In the case of the latter, a cyllization temperature of about ambient temperature is preferred.

The hydrolysis of a 3-(1-alkanoyl-4-piperidyl)-1,2-benzisoxazole 13 to a 3-(1-unsubstituted-4-piperidyl)-1,2-benzisoxazole 17 is conducted by methods known per se involving a mineral acid such as hydrochloric acid, hydrobromic acid and the like, at a reaction temperature between about ambient temperature and the reflux temperature of the hydrolysis mixture. Hydrochloric acid at the reflux temperature is preferred. When hydrobromic acid, e.g., 48% hydrobromic acid, is employed, aromatic alkoxy groups, i.e., anisole moieties, are cleaved to hydroxyl groups, i.e., phenolic moieties.

The condensation of a 4-chloro-N-alkylpiperidine 19 with a benzonitrile 20 is effected by conventional Grignard techniques. Typically, the chloropiperidine 19 is dissolved or suspended in an ethereal solvent such as tetrahydrofuran; magnesium is added and the mixture is heated under reflux until the reaction is complete. An initiator such as ethyl bromide may be employed to facilitate the reaction.

The cyclization of a 1-alkyl-4-benzoylpiperidine 21 to a 3-(1-alkyl-4-piperidyl)-1,2-benzisoxazole 22 is performed by treating the benzoylpiperidine 21 with hydroxylamine as a salt thereof with a base in a suitable solvent. Among salts of hydroxylamine, there may be mentioned the hydrochloride, hydrobromide and sulfate, the hydrochloride being preferred. Bases include alkali metal hydroxides such as lithium hydroxide, sodium hydroxide, potassium hydroxide, and the like, and alkaline like, and alkaline earth hydroxides such as calcium hydroxide, magnesium hydroxide and the like. The cyclization temperature is not critical. To promote the reaction, however, it is desirable to heat the system under reflux. The intermediate oxime of 21 may be isolated, and is isolated in certain cases, and cyclized to 22. The cyclization is accomplished with a hydride such as sodium or potassium hydride in a mixture of a polar aprotic solvent such as dimethylacetamide, dimethylformamide or hexamethylphosphoramide and an ethereal solvent such as tetrahydrofuran, dioxide or 1,2-dimethoxyethane at an elevated temperature of about 70° to 110° C. Sodium hydride in tetrahydrofurandimethylformamide at a temperature of about 90° C. is the preferred reaction condition.

A 3-(1-unsubstituted-4-piperidyl)-1,2-benzisoxazole 18 is also prepared by hydrolyzing a 1-alkanoyl-4-benzoylpiperidine 11 to a 1-unsubstituted 4-benzoylpiperidine 12, acylating a 4-benzoylpiperidine 12 to a benzoyl-1-piperidine carboxylic acid phenyl methyl ester 13, cyclizing a benzoylpiperidine ester 13 to a benzisoxazolylpiperidine carboxylic acid ester 25, and hydrolyzing an ester 25 to a 1-unsubstituted compound 18. See Schemes A and D.

The hydrolysis of a 1-alkanoyl-4-benzoylpiperidine 11 to a 1-unsubstituted 4-benzoylpiperidine 12 is performed by methods well-known in the art, involving, for example, treatment of an alkanoyl derivative 11 with a mineral acid such as hydrochloric acid at elevated temperatures at or about the reflux temperature of the reaction temperature.

The acylation of a 1-unsubstituted benzoylpiperidine 12 is conveniently accomplished by treating the piperidine 12 with a benzyl haloformate, for example, benzyl chloroformate or benzyl bromoformate, in a halocarbon such as dichloromethane, chloroform or the like, in the presence of an acid scavenger such as an alkali carbonate or alkali bicarbonate such as potassium carbonate or sodium bicarbonate. Benzyl chloroformate in dichloromethane containing sodium bicarbonate is the preferred reagent system when Z is hydroxy. Stronger bases such as carbonates are preferred when Z is halogen.

The cyclization of a benzoylpiperidine ester 13 to a benzisoxazole 25 is effected by the processes hereinbefore described, preferrably, by the sequence involving the conversion of the ketone function to the oxime acylate thereof, and base treatment.

The hydrolysis of an ester 25 to a 1-unsubstituted 18 is conducted by art-known methods, involving the use of a hydrogen halide such as hydrogen chloride or hydrogen bromide in an alkanoic acid such as formic acid, acetic acid or propionic acid. Hydrogen bromide in acetic acid is preferred.

Similarly, a 3-(1-unsubstituted-4-piperidyl)1,2-benzisoxazole 18 may be prepared by benzylating a 1-unsubstituted 4-benzoylpiperidine 12 to a 1-benzyl-4-benzoylpiperidine 14, cyclizing a benzoylpiperidine 14 to a benzisoxazole 26 and cleaving the 1-benzyl group of 26 to 1-unsubstituted compound 18.

The benzylation of a 1-unsubstituted piperidine 12 is performed by means of a benzyl halide such as benzyl chloride or benzyl bromide, benzyl bromide being preferred, in the presence of a base, suspended or dissolved in a polar aprotic solvent. Suitable bases include alkali carbonates and bicarbonates, such as, for example, sodium and potassium carbonate, and sodium and potassium bicarbonate. Suitable polar aprotic solvents include dimethylacetamide, dimethylformamide and hexamethylphosphoramide. Sodium bicarbonate and dimethylformamide are the preferred base and solvent.

Cyclization processes hereinbefore described, i.e., cyclization processes 11→15, 16→17, and 21→22, may be employed to convert a benzylpiperdine 14 to benzisoxazole 26. The sequence involving the O-acyloxime may be preferred.

The cleavage of a 3-(1-benzyl-4-piperidyl)-1,2-benzisoxazole 26 to a 1-unsubstituted compound 18, i.e., the debenzylation of 26, may be achieved by the dealkylation process described immediately below.

A 3-(1-unsubstituted-4-piperidyl)-1,2-benzisoxazole 18 is prepared by dealkylation of a 3-(1-unsubstituted-4-piperidyl)-1,2-benzisoxazole 22 as illustrated in Scheme C. The dealkylation is readily performed by treating an alkylpiperidine 22 with a phenyl haloformate such as phenyl chloroformate or phenyl bromoformate in an appropriate solvent in the presence of a suitable base to afford a quaternary piperidinium salt 23, for example, 4-(4-fluoro-1,2-benzisoxazole-3-yl)-1-methyl-1-phenoxycarbonyl piperidinium chloride, which without isolation, is transformed to a piperidine carboxylic acid phenyl ester 24 and hydrolyzed to 1-unsubstituted compound 18.

Among suitable bases, there may be mentioned alkali and alkaline earth carbonates and bicarbonates such as, for example, sodium and potassium carbonate and sodium and potassium bicarbonate, and calcium carbonate and bicarbonate. Potassium carbonate is preferred. Appropriate solvents include halocarbons such as dichloromethane, chloroform, dichloroethane and the like, polar aprotic substances such as dimethylacetamide, dimethylformamide and hexamethylphosphoramide, and aromatics such as benzene, toluene, xylene and the like. Aromatics are preferred; toluene is most preferred. The reaction temperature is not critical. An elevated temperature is, however, desirable to promote the loss of the elements of RU from the quaternary salt. The hydrolysis of a piperidine carboxylic acid phenyl ester 24 to 1-unsubstituted piperidine 18 is performed by conventional techniques employing alkali hydroxides such as potassium hydroxide in an aqueous alkanol such as aqueous ethanol at the reflux temperature of the reaction system.

Derivatives of the parent system, i.e., derivatives of the 3-(4-piperidyl)-1,2-benzisoxazole system, are prepared from a nitrogen unsubstituted compound 18 by the processes outlined in Reaction Schemes E, F and G.

To prepare a 3-(1-alkenyl-4-piperidyl)-1,2-benzisoxazole 28, a 3-(1-unsubstituted-4-piperidyl)-1,2-benzisoxazole 18 is contacted with an alkenyl halide 27 in a suitable solvent in the presence of an acid acceptor. Suitable solvents include polar aprotic substances such as dimethylacetamide, dimethylformamide and hexamethylphosphoramide. Suitable acid acceptors include alkali carbonates and alkali bicarbonates such as potassium carbonate and sodium bicarbonate. Potassium iodide and elevated temperatures within the range of 75°–100° C. may be employed to promote the alkenylation.

Alternatively, a 3-(1-alkenyl-4-piperidyl)-1,2-benzisoxazole 28 may be elaborated by alkenylation of oxime 29, prepared from a 1-unsubstituted benzoylpiperidine 12 by hereinbefore described methods, according to processes utilized for the conversion of piperidylbenzisoxazole 18 to N-alkenylpiperidylbenzisoxazole 28, followed by cyclization, also by techniques disclosed herein.

To synthesize a 3-(1-phenylalkyl-4-piperidyl)-1,2-benzisoxazole 34 or a 3-(1-cycloalkylalkyl-4-piperidyl)-1,2-benzisoxazole 31, the 1-unsubstituted compound 18 is treated, respectively, with a phenylalkyl halide 32 or a cycloalkylalkyl halide 33 in a polar aprotic solvent such as dimethylacetamide, dimethylformamide and hexamethylphosphoramide, in the presence of an acid scavenger such as sodium or potassium carbonate or bicarbonate. A promotor such as potassium iodide may be used and the reaction may be conducted at an elevated temperature of 50°–100° C. to facilitate the conversion. Potassium carbonate in dimethylformamide at 60°–80° C. are the preferred reaction conditions.

To introduce the dialklaminoalkyl group into the 1-unsubstituted piperidylbenzisoxazole 18, i.e., to prepare a 3-(1-dialkylaminoalkyl-4-piperidyl)-1,2-benzisoxazole 36, one treats a piperidylbenzisoxazole 18 with a dialkylaminoalkyl halide 35 in an alkanol, for example, methanol, ethanol, 2-propanol, 1-butanol and the like, n-butanol being preferred, in the presence of an acid acceptor such as an alkali carbonate (potassium carbonate) or bicarbonate (sodium bicarbonate) as in similar akylations, a promotor such as potassium iodide and elevated temperatures, for example, the reflux temperature of the reaction system may be used to facilitate the reaction.

To prepare a 3-(1-hydroxy-4-piperidyl)-1,2-benzisoxazole 38, a 1-unsubstituted compound 18 is treated with benzoyl peroxide in an aromatic solvent such as benzene, toluene or xylene, benzene being preferred, in the presence of a base such as an alkali metal carbonate or bicarbonate, for example, potassium carbonate or sodium bicarbonate, potassium carbonate being preferred, to yield a 3-(1-benzoyloxy-4-piperidyl)-1,2-benzisoxazole 37, which is hydrolyzed by methods known per se such as an alkali hydroxide (sodium hydroxide) in an aqueous alkanol (aqueous ethanol) to provide the 1-hydroxy compound 38. Neither the oxidation nor hydrolysis temperatures are narrowly critical. At about ambient temperature, the oxidation proceeds at a reasonable rate, and at the reflux temperature of the reaction system, the hydrolysis also proceeds at a convenient rate.

To furnish a 3-(1-cyano-4-piperidyl)-1,2-benzisoxazole 43, ($R^{13}$ is alkyl), a 3-(1-alkyl-4-piperidyl)-1,2-benzisoxazole 40 is treated with a cyanogen halide such as cyanogen bromide 41 or cyanogen chloride, preferably cyanogen bromide, in a halocarbon such as dichloromethane, trichloromethane or dichloroethane, preferably dichloromethane, in the presence of an acid scavenger such as sodium or potassium carbonate or sodium or potassium bicarbonate, preferrably potassium carbonate, to afford an alkylcyanopiperidinium salt 42, for example, 5-methyl-1,2-benzisoxazol-3-yl)-1-cyano-1-methyl-piperidinium chloride, which loses the elements of an alkylhalide ($R^{13}U$) to form a 1-cyano derivative 43. The reaction proceeds readily at moderate temperatures. To facilitate the conversion, however, elevated temperatures, i.e., the reflux temperatures of the system, are employed.

Alternatively, a 3-(1-unsubstituted-4-piperidyl)-1,2-benzisoxazole 40 ($R^{13}$ is hydrogen) is treated with a cyanogen halide 41 such as cyanogen bromide or cyanogen chloride, preferrably cyanogen bromide, to afford a 1-cyano derivative 43. The conversion is performed in a halocarbon such as dichloromethane, trichlormethane or dichloroethane, preferably trichoromethane, in the presence of an acid acceptor such as sodium or potassium carbonate, or sodium and potassium bicarbonate, preferrably sodium bicarbonate. A promoter such as potassium iodide may be employed to facilitate the conversion. An elevated temperature, for example, the reflux temperature of the system, may also be employed to assure a reasonable rate of conversion.

A 3-(1-cyano-4-piperidyl)-1,2-benzisoxazole 43 may be hydrolyzed to a 3-(1-unsubstituted-4-piperidyl)-1,2-benzisoxazole 40 ($R^{13}$ is hydrogen) by conventional methods involving acidic or basic reaction conditions. See, for example, R. B. Wagner and Harry P. Zook, "Synthetic Organic Chemistry", John Wiley and Sons, Inc., New York, N.Y., page 680 and the reference cited therein.

To synthesize a 3-(1-cyanomethyl-4-piperidyl)-1,2-benzisoxazole 45, a 1-unsubstituted piperidine 40 ($R^{13}$ is hydrogen) is contacted with a haloacetonitrile 44 such as choro- or bromoacetonitrile, preferrably chloroacetonitrile, in a polar aprotic solvent such as dimethylformamide, dimethylacetamide or hexamethylphosphoramide, preferably dimethylformamide, in the presence of an acid acceptor such as potassium or sodium bicarbonate or potassium or sodium carbonate, preferrably potassium carbonate, and a promotor such as postassium iodide. To assure completion of the conversion, an elevated temperature within the range of about 50° to 100° C. may be employed. A temperature within the range of about 80° to 85° is preferred.

The 3-(4-piperidyl)-1,2-benzisoxazoles of the present invention are useful as analgetics due to their ability to alleviate pain in mammals. The analgetic utility is demonstrated in the phenyl-p-quinone writhing assay in mice, a standard assay for analgesia [Proc. Soc. Exptl. Biol Med., 95 729 (1957)]. Thus, for instance, the subcutaneous dose effecting an approximately 50% inhibition of writhing ($ED_{50}$) in mice produced in this assay is as follows:

| Compound | $ED_{50}$ mg/kg |
| --- | --- |
| 3-(1-methyl-4-piperidyl)-1,2-benzisoxazole hydrochloride | 0.415 |
| 3-(4-piperidyl)-1,2-benzisoxazole hydrochloride | 0.517 |
| 3-(1--phenylethyl-4-piperidyl)-1,2-benzisoxazole hydrochloride | 0.386 |
| 3-(1-allyl)-4-piperidyl)-1,2-benzisoxazole hydrochloride | 1.06 |
| 3-[1-(3-dimethylaminopropyl)-4-piperidyl]-1,2-benzisoxazole difumarate | 7.4 |
| 3-(1-methyl-4-piperidyl)-5-methyl-1,2-benzisoxazole fumarate | 0.566 |
| 3-(4-piperidyl)-6-fluoro-1,2-benzisoxazole hydrochloride | 1.79 |
| 3-(4-piperidyl)-6-chloro-1,2-benzisoxazole hydrochloride | 5.6 |
| 3-1-(allyl-4-piperidyl)-6-fluoro-1,2-benzisoxazole hydrochloride | 0.455 |
| propoxyphene (standard) | 3.9 |
| pentazocine (standard) | 1.3 |

Analgesia production is achieved when the present 3-(4-piperidyl)-1,2-benzisoxazoles are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. The 3-(4-piperidyl)-1,2-benzisoxazoles of the present invention, while effective themselves, may be formulated and administered in the form of their pharmacetucally acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of the invention may be administered orally, for example, with an inert diluent or with an edible carrier. They may be enclosed in gelatin capsules or compressed into tablets. For the purpose of oral therapeutic administration, the aforesaid compounds may be incorporated with excipient and used in the form of tablets, troches, capsules, elixirs, suspensions, syrups, wafers, chewing gums and the like. These preparations should contain at least 0.5%) of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0-300 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, Primogel, corn starch and the like; a lubricant such as magnesium stearate or Sterotes; a glidant such as colloida silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Scheme A

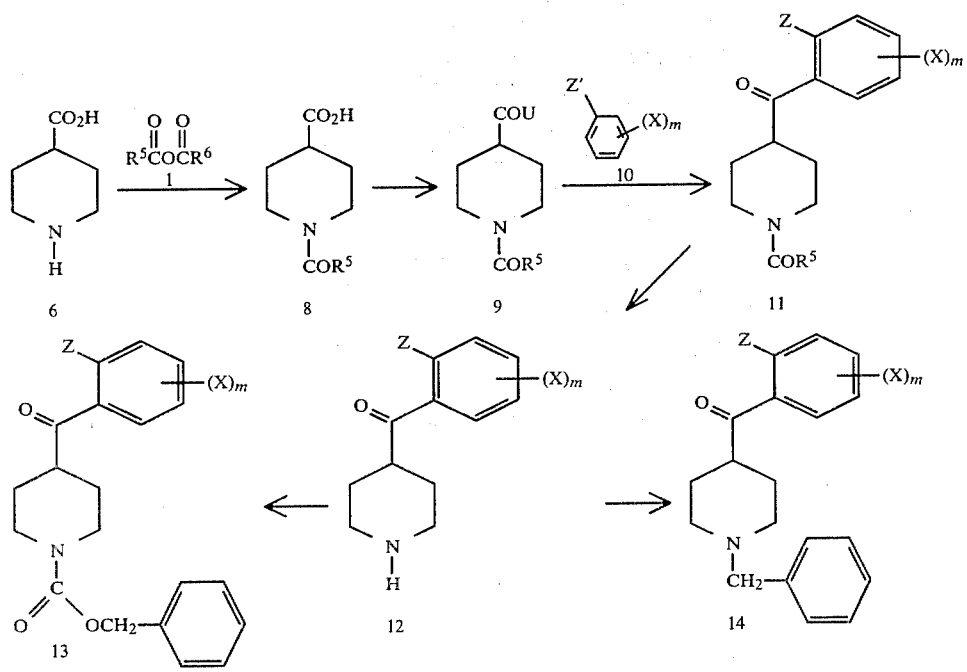

Wherein $R^5$ is hydrogen or alkyl; $R^6$ is alkyl; U is halogen; X is hydrogen, alkyl, alkoxy, halogen or hydroxy; $Z'$ is halogen or alkoxy, Z is halogen or hydroxy; and m is 1 or 2.

Scheme B
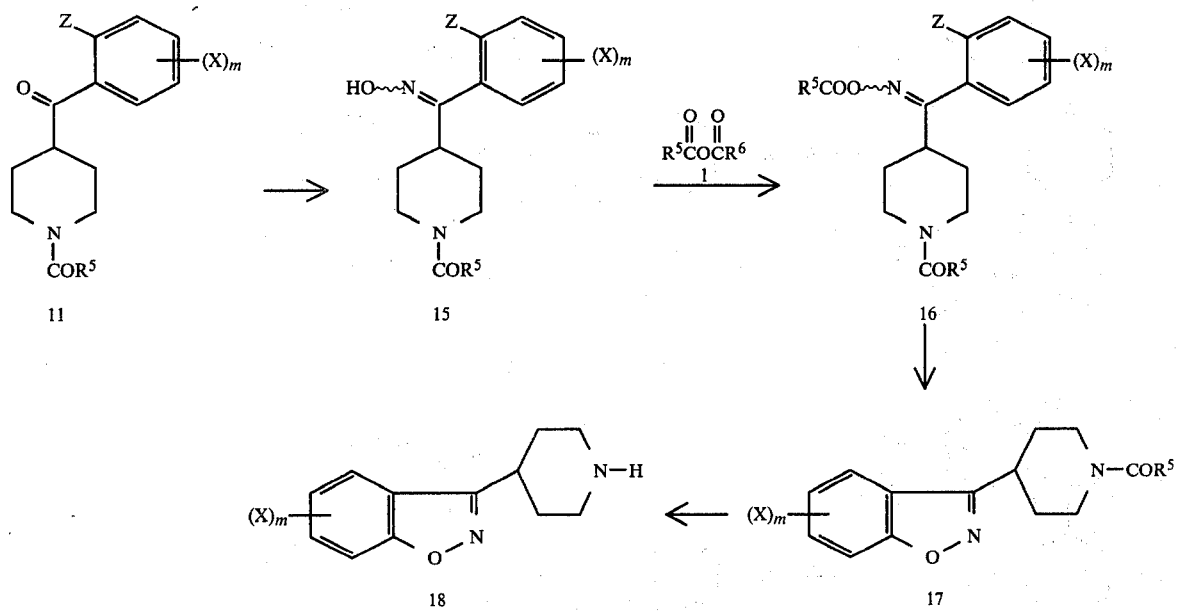
Wherein $R^5$ is hydrogen or alkyl; $R^6$ is alkyl; X is hydrogen, alkyl, alkoxy, halogen or hydroxy; Z is hydroxy; and m is 1 or 2.
Scheme C
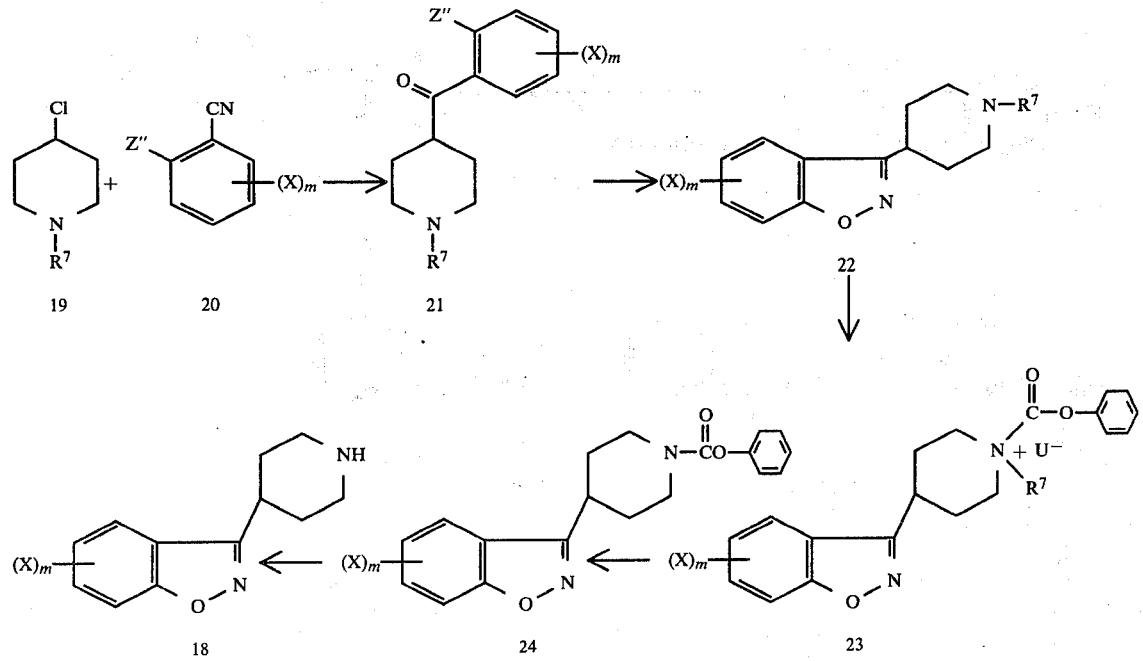
Wherein $R^7$ is alkyl or alkanoyl; U is halogen; X is hydrogen, alkyl, alkoxy, halogen or hydroxy; $Z''$ is halogen; and m is 1 or 2.

Scheme D
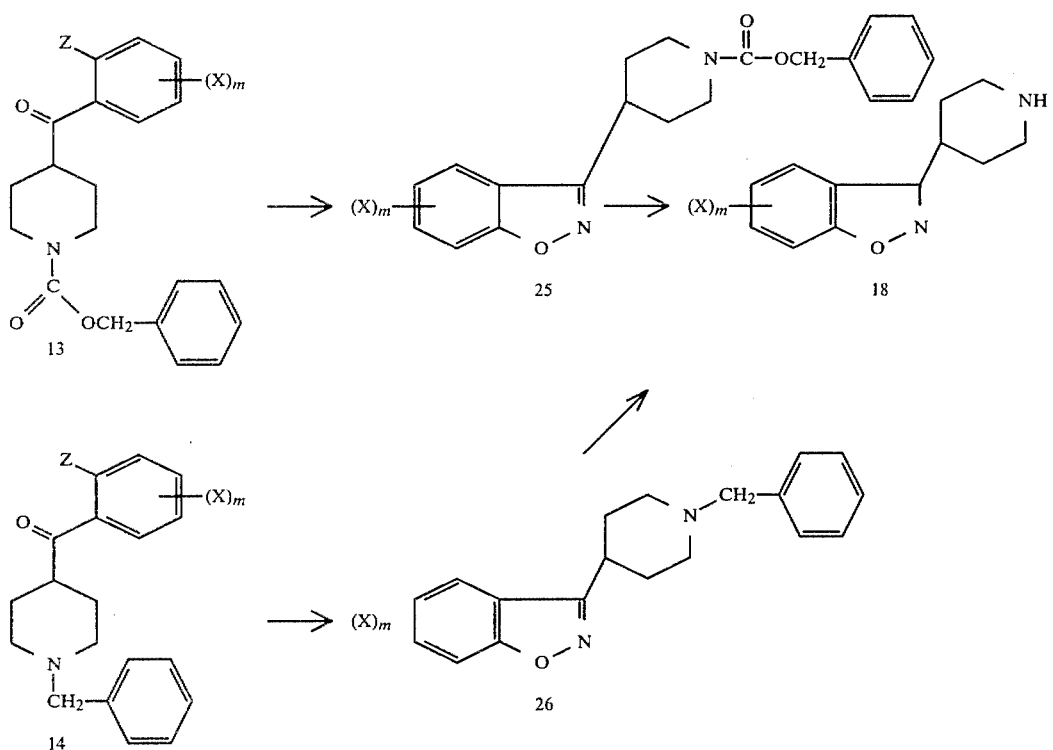
Wherein X is hydrogen, alkyl, alkoxy, halogen or hydroxy; Z is halogen or hydroxy; and m is 1 or 2.
Scheme E
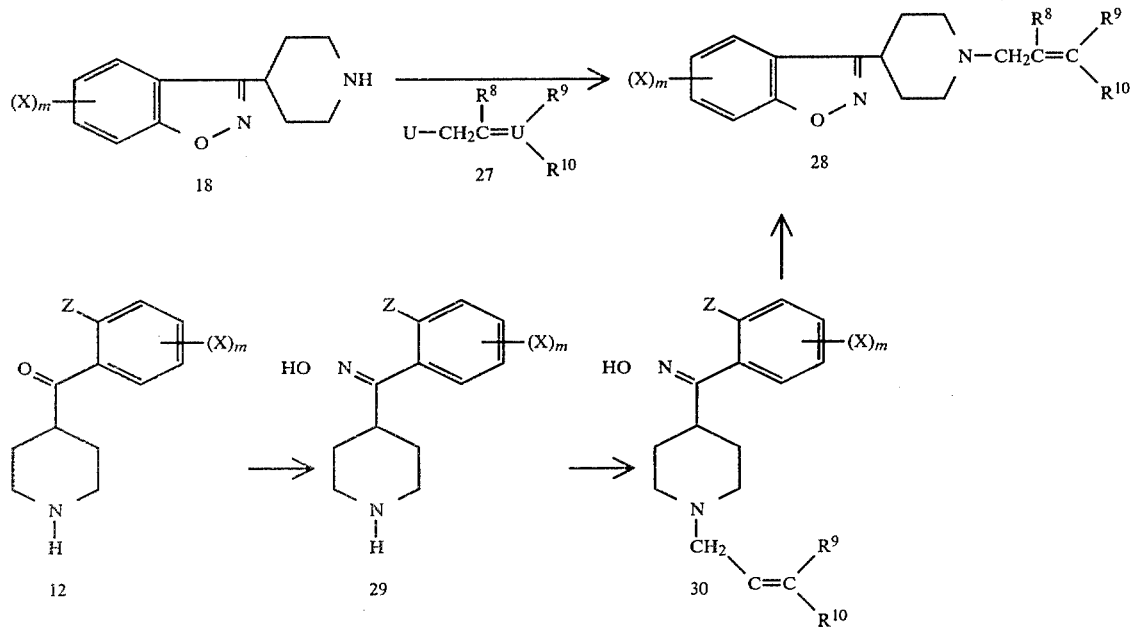
Wherein $R^8$, $R^9$ and $R^{10}$ are each independently hydrogen or alkyl; U is halogen; X is hydrogen, alkyl, alkoxy, hydroxy or halogen; Z is halogen or hydroxy; and m is 1 or 2.

Scheme F

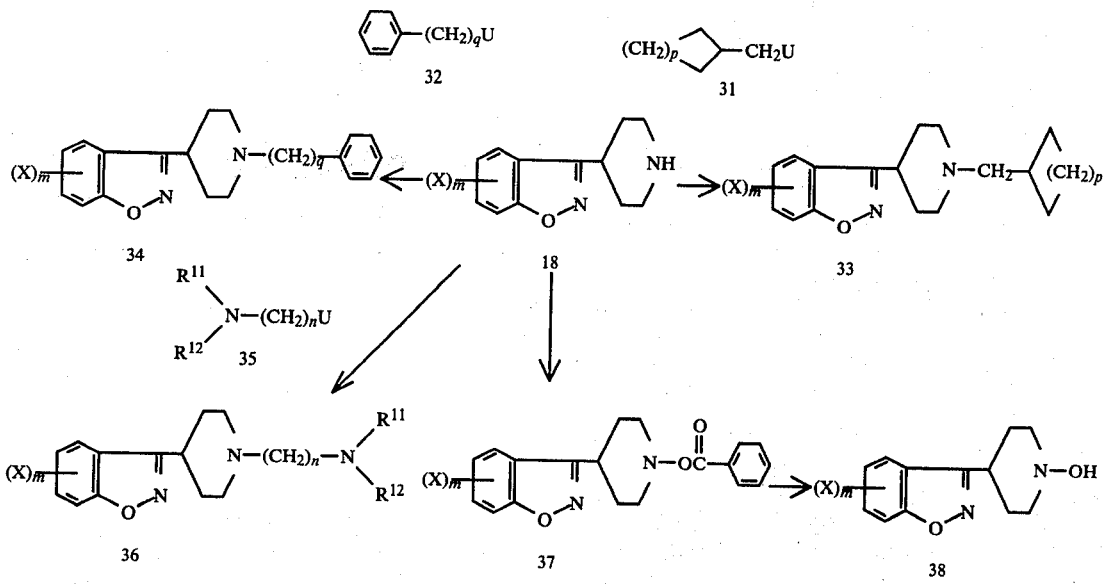

Wherein $R^{11}$ and $R^{12}$ are each independently alkyl; U is halogen; X is hydrogen, alkyl, alkoxy, halogen and hydroxy; m is 1 or 2; n is 1 or 2; p is 0 to 4; and q is 1 or 2.

Scheme G

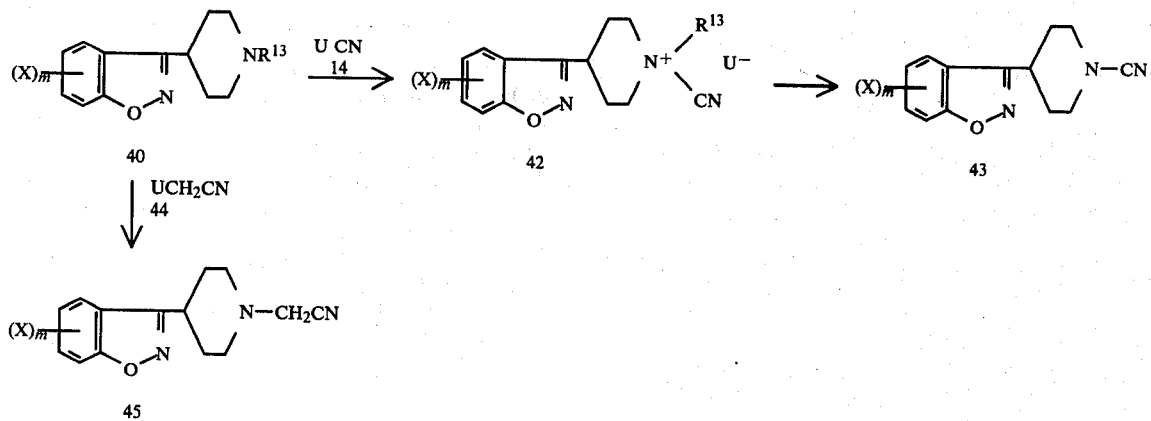

Wherein $R^{13}$ is hydrogen or alkyl; U is halogen; and X is hydrogen, alkyl, alkoxy, halogen or hydroxy.

The following examples are for illustrative purposes only and are not to be construed as limiting the invention. All temperatures are given in degrees centigrade (°C.).

EXAMPLE 1

1-Methyl-4-(2-chloro-5-methylbenzoyl)piperidine fumarate

To a suspension of 10.8 g of magnesium in 30 ml of anhydrous tetrahydrofuran was added a crystal of iodine followed by a few mls of 4-chloro-N-methylpiperidine. The reaction was initiated with a hot air gun and 54.3 g of 4-chloro-N-methylpiperidine in 100 ml of anhydrous tetrahydrofuran was added dropwise at a rate maintaining reflux. Upon completion of the addition, the reaction mixture was refluxed for 3 hrs and then 50 g of 2-chloro-5-methylbenzonitrile in 225 ml of tetrahydrofuran was added dropwise. Upon completion of the addition, the reaction mixture was heated under reflux for an additional 2 hrs and stirred overnight at room temperature. The reaction mixture was poured into a solution of 100 g of ammonium chloride in 1 l of water, heated on a steam bath for 2 hrs, cooled, extracted with ether and dried over anhydrous sodium sulfate. The solvent was removed under reduced pressure and the residue was distilled (0.2 mm, 115°–125°) to give 54 g (56%) of product. The fumarate salt was made by dissolving 1 g of product in approximately 5 ml of acetonitrile and adding 0.5 g of fumaric acid. The suspension was stirred for 1 hr, filtered and the filter cake was recrystallized twice from ethanol-ether to give the salt, mp, 148°–150°.

ANALYSIS: Calculated for $C_{14}H_{18}ClNO \cdot C_4H_4O_4$: 58.77%C, 6.03%H, 3.81%N. Found: 58.57%C, 5.89%H, 3.82%N.

EXAMPLE 2

4-(2,4-Difluorobenzoyl)-N-formylpiperidine a. To the mixed anhydride of formic acid and acetic acid, prepared by dropping 334 ml of formic acid (98%) into 666 ml of acetic anhydride, over 15 mins at 20°, removing the ice bath and allowing the reaction mixture to warm up to 55°–60° and after 30 mins, cooling the reaction mixture to 15°, was added, over 5 mins, with stirring and cooling in an ice bath, 129 g of isonipecotic acid. After stirring in an ice bath for 16 hrs, the reaction mixture was distilled under vacuum at 80° until crystals formed. The residue was diluted with 1 l of isopropyl ether. The precipitate was collected, washed twice with 400 ml isopropyl ether and dried over potassium hydroxide under vacuum. Recrystallization from isopropyl ether gave 120 g (76.3%) of N-formylisonipec-otic acid, mp, 140°.

b. To 100 ml of freshly distilled thionyl chloride was added 30 g of N-formylisonipecotic acid at 0°. After the addition was complete, 2 ml of acetic anhydride was added and the solution was stirred at 20° for three hrs. The reaction mixture was diluted with 3 400-ml portions of petroleum ether, bp, 60°–80°. The resulting solid was collected, washed with 50 ml of ether and dried under vacuum over phosphorous pentoxide to yield 33.5 g (100%) of N-formylisonipecotic acid chloride.

c. To a slurry of 39 g of aluminum chloride and 120 ml of 1,3-difluorobenzene was added dropwise, with stirring, 30 g of N-formylisonipecotic acid chloride. The reaction mixture was stirred under reflux for two hrs and poured into 1 l of ice-water. The mixture was extracted with 4 350-ml portions of chloroform. The combined organic extracts were washed with 2 300-ml portions of water, dried, filtered and evaporated. Trituration with petroleum ether and washing with ether at 0°, yielded 14 g (32.3%) of product, mp, 75°.

ANALYSIS: Calculated for $C_{13}H_{13}F_2NO_2$: 61.63%C, 5.17%H, 5.53%N. Found: 61.42%C, 5.07%H, 5.42%N.

EXAMPLE 3

1-Acetyl-4-(2-hydroxy-5-methoxybenzoyl)piperidine

To a stirred mixture of 60.0 g of isonipecotic acid and 290 ml of 1,2-dichloromethane, at 40°, was added dropwise, 27 ml of thionyl chloride, dissolved in 27 ml of dichloroethane. After 50% of the thionyl chloride had been added, the temperature was raised to 65°. After complete addition of the thionyl chloride, the reaction mixture was stirred at 65° for 1 hr. The reaction mixture was cooled to 20° and 48.6 g of 1,4-dimethoxybenzene was added, followed by the slow addition of 93.6 g of aluminum chloride. The solution was heated under reflux for 4 hrs, the dichloroethane was decanted from the insoluble complex, and concentrated hydrochloric acid was added. The acid hydrolysate was added to the dichloroethane solution and the mixture was extracted three times with chloroform. The organic extract was washed with water, dried over anhydrous magnesium sulfate and the solvent was removed in vacuo to give an oil. The oil was scratched with a glass rod until crystallization was effected. The solid was collected to yield 87.0 g of product. Recrystallization twice from isopropyl ether gave an analytically pure product, mp, 93°–94°.

ANALYSIS: Calculated for $C_{15}H_{19}NO_4$: 64.96%C, 6.91%H, 5.05%N. Found: 64.91%C, 6.90%H, 5.00%N.

EXAMPLE 4

1-Acetyl-4-(2,4-difluorobenzoyl)piperidine

To a slurry of 6.6 g of aluminum chloride and 20 ml of 1,3-difluorobenzene was added, with stirring at ambient temperature, 5.0 g of N-acetylisonipecotyl chloride. The reaction mixture was heated under reflux for 1½ hrs and then poured onto 100 ml of ice and water. The mixture was extracted with chloroform. The chloroform fractions were combined, washed with water and dried over anhydrous magnesium sulfate and filtered. Evaporation of the filtrate gave an oil. Trituration of the oil with pentane gave 4.65 g (65.9%) of product, mp, 100°–102°.

ANALYSIS: Calculated for $C_{14}H_{15}F_2NO_2$: 62.91%C, 5.66%H, 5.24%N. Found: 62.82%C, 5.43%H, 5.21%N.

EXAMPLE 5

1-Acetyl-4-(2-hydroxy-4,5-dimethoxybenzoyl)piperidine

To a stirred mixture of 20.0 g of isonipecotic acid and 90 ml of 1,2-dichloroethane at 40°, was added dropwise 9 ml of thionyl chloride, dissolved in 10 ml of dichloromethane. After 50% of the thionyl chloride had been added, the temperature was raised to 60° for 1 hr. The reaction mixture was cooled to ambient temperature and 19.6 g of 1,2,4-trimethoxybenzene was added, followed by the slow addition of 31.2 g of aluminum chloride. The reaction mixture was refluxed for 4 hrs, the dichloroethane decanted from the insoluble complex and concentrated hydrochloric acid was added. The acid hydrolsate was added to the previously decanted dichloroethane and the mixture was extracted with dichloromethane. The solvent was removed in vacuo to give a solid which recrystallized from isopropanol to yield 19.7 g (54.&%) of product, mp, 162°–164°.

ANALYSIS: Calculated for $C_{16}H_{21}NO_5$: 62.52%C, 6.89%H, 4.56%N. Found: 62.47%C, 6.87%H, 4.55%N.

EXAMPLE 6

1-Acetyl-4-(5-fluoro-2-hydroxybenzoyl)piperidine

To a stirred mixture of 20.0 g of 1-acetylisonipecotic acid and 90 ml of 1,2-dichloroethane, at 40°, was added dropwise, 27 ml of thionyl chloride, dissolved in 9 ml of dichloroethane. After 50% of the thionyl chloride had been added, the temperature was raised to 65°. After complete addition of the thionyl chloride, the reaction mixture was stirred at 65° for 1 hr. After cooling to ambient temperature, 14.8 g of 4-fluoroanisole was added, followed by the slow addition of 31.2 g of aluminum chloride. The solution was heated under reflux for 4 hrs and then poured into ice-water. The mixture was extracted two times with chloroform. The extract was washed with water, dried over anhydrous magnesium sulfate and the solvent was removed in vacuo to give a solid. The solid was triturated with ether and recrystallized from toluene-cyclohexane to afford 16.5 g (53%) of product, mp, 121°–123°. An analytical sample was obtained by recrystallization from toluene-cyclohexane, mp, 121°–123°.

ANALYSIS: Calculated for $C_{14}H_{16}FNO_3$: 63.38%C, 6.08%H, 5.28%N. Found: 63.20%C, 6.01%H, 5.11%N.

EXAMPLE 7

1-Acetyl-4-(2,4-dichlorobenzoyl)piperidine

To a stirred slurry of 25 g of aluminum chloride in 147 g of 1,3-dichlorobenzene was added 18.97 g of N-acetylisonipecotyl chloride. The reaction mixture was heated to ca. 70°. Thereafter the reaction mixture was heated at ca. 120° for 2.5 hrs, with stirring. Unreacted dischlorobenzene was distilled in vacuum at 70° (16 mm). The residue was decomposed with 1 l of ice-water and 10 ml concentrated hydrochloric acid. The oil was isolated by decantation, washed twice with ca. 300 ml of water and dissolved in 300 ml of dichloromethane. The dichloromethane extract was washed with 200 ml of water, with 100 ml 2N sodium hydroxide solution, two times with 200 ml water and dried over anhydrous magnesium sulfate. The dichloromethane was distilled to yield 16.2 g (54.0%) of product. An analytical sample was prepared by dissolving the oil in dichloromethane, treating with charcoal, filtering and eluating with dichloromethane from a column of aluminum oxide (Woelm, neutral, act. st. II) and removing the solvent.

ANALYSIS: Calculated for $C_{14}H_{15}C_{12}NO_2$: 55.99%C, 5.04%H, 4.66%N, 23.62% Cl. Found: 55.70%C, 5.03%H, 4.58%N, 23.70%Cl.

EXAMPLE 8

4-(2,4-Difluorobenzoyl)piperidine fumarate

A 3.0 g sample of 1-acetyl-4-(2,4-difluorobenzoyl)-piperidine in 20 ml of 6N hydrochloric acid was stirred for 3 hrs at 130°. The reaction mixture was cooled, extracted with ether and the acidic solution was basified with 25% sodium hydroxide solution. The basic solution was extracted with dichloromethane filtrate and the combined extracts were dried over anhydrous magnesium sulfate. The mixture was filtered and then evaporated to an oil which was converted to the fumarate salt. Yield 1.30 g (34.0%), mp 190°-192°.

ANALYSIS: Calculated for $C_{12}H_{13}F_2NO \cdot C_4H_4O_4$: 56.30%C, 5.02%H, 4.10%N. Found: 56.23%C, 5.04%H, 4.09%N.

EXAMPLE 9

4-(2-Hydroxy-4-methoxybenzoyl)piperidine hydrochloride

To a round-bottom flask, equipped with a condenser and mechanical stirrer, was added 25.0 g of 1-acetyl-4-(2-hydroxy-4-methoxybenzoyl)piperidine and 148 ml of 6N hydrochloric acid. The reaction mixture was stirred under reflux for 6 hrs and overnight at ambient temperature. The precipitate was collected, washed with acetone and recrystallized twice from ethanol to yield 16.70 g of product, mp, 264°-266°.

ANALYSIS: Calculated for $C_{13}H_{17}O_3N \cdot HCl$: 57.47%C, 6.65%H, 5.16%N. Found: 57.26%C, 6.71%H, 5.06%N.

EXAMPLE 10

4-(2-Hydroxy-5-methoxybenzoyl)piperidine hydrobromide

A mixture of 10.0 g of 1-acetyl-4-(2-hydroxy-5-methoxybenzoyl)-piperidine and 60 ml of 6N hydrochloric acid was heated under reflux for 6 hrs. The solution was made basic with ammonium hydroxide and extracted with dichloromethane. Evaporation of the dichloromethane in vacuo yielded 8.2 g of an oil. A 3.5 g sample of the oil was converted to the hydrobromide salt by dissolving the oil in anhydrous ethanol and adding saturated hydrogen bromide-ether solution. The salt was recrystallized from ethanol-ether to yield 2.8 g (59.5%) of product as the hydrobromide, mp, 247°-249°.

ANALYSIS: Calculated for $C_{13}H_{17}NO_3 \cdot HBr$: 49.38%C, 5.74%H, 4.43%N. Found: 49.93%C, 4.84%H, 4.45%N.

EXAMPLE 11

4-(2,4-Dichlorobenzoyl)piperidine hydrochloride

A solution of 4-(2,4-dichlorobenzoyl)-N-acetylpiperidine in 300 ml of 6N hydrochloric acid was heated under reflux for 4 hrs. The solution was cooled in an ice bath and basified with 25% sodium hydroxide. The basic solution was extracted with 300 ml of dichloromethane. The organic phase was washed with brine, dried over anhydrous sodium sulfate and concentrated in vacuo to give 31.6 g of solid. A 6.0 g sample of the solid was dissolved in 100 ml of ethanol, with cooling in an ice bath. To the cold solution was added dropwise 10 ml of ether saturated with hydrogen chloride. The salt was collected and washed with ether and recrystallized 2 times from a 2:1 ethanol-ether to afford 2.2 g (32%) of product as the hydrochloride, mp 215°-217°.

ANALYSIS: Calculated for $C_{12}H_{13}C_{12}NO \cdot HCl$: 48.92%C, 4.79%H, 4.75%N. Found: 49.01%C, 4.80%H, 4.65%N.

EXAMPLE 12

4-(2-Hydroxy-4-methoxybenzoyl)-1-piperidine carboxylic acid, phenylmethyl ester To a stirred, ice-cooled mixture of 36.1 g of 4-(2-hydroxy-4-methoxybenzoyl)piperidine, 16.3 g of sodium bicarbonate and 350 ml of dichloromethane, was added dropwise 22.9 ml of benzyl chloroformate in dichloromethane. After the addition was complete, the mixture was stirred at ambient temperature for 1.5 hrs, filtered and the filtrate concentrated to an oil. The oil crystallized. The crystals were collected, washed with hexane and dried to yield 42.4 g (76.5%) of product. Recrystallization from isopropanol gave the analytical sample, mp, 89°-91°.

ANALYSIS: Calculated for $C_{21}H_{23}NO_5$: 68.28%C, 6.28%H, 3.79%N. Found: 68.23%C, 6.30%H, 3.71%N.

EXAMPLE 13

1-Benzyl-4-(2-hydroxy-4-methoxybenzoyl)piperidine

A mixture of 14.50 g of 4-(2-hydroxy-4-methoxybenzoyl)piperidine, 6.40 ml of benzyl bromide, 10.20 g of sodium bicarbonate and 74.0 ml of dimethylformamide was stirred at 60° for 15 hrs. The reaction mixture was poured into 250 ml of water and a precipitate formed. The precipitate was collected, washed with water and recrystallized from ethanol to yield 10.0 g (57.4%) of product, mp, 123°-125°.

ANALYSIS: Calculated for $C_{20}H_{23}NO_3$: 73.84%C, 7.08%H, 4.31%N. Found: 73.76%C, 7.14%H, 4.26%N.

EXAMPLE 14

1-Methyl-4-(2,6-difluorobenzoyl)piperidine

A 6.60 g sample of magnesium was added to a 3-neck, round-bottom flask equipped with a condenser, mechanical stirrer and addition funnel. The apparatus was flame dried and cooled under a stream of nitrogen. About 1 ml of ethyl bromide was dissolved in 30 ml of tetrahydrofuran and added to the magnesium. The mixture was heated to reflux and 30.0 g of 4-chloro-N-methylpiperidine, dissolved in 75 ml of tetrahydrofuran, was added. The addition was made at such a rate to achieve a moderate reflux. After the addition was complete, the reaction mixture was heated under reflux for 1 hr. The reaction mixture was cooled to 0° and 31.4 g of 2,6-difluorobenzonitrile, dissolved in 100 ml of tetrahydrofuran, was added dropwise through the addition funnel. After the addition was complete, the mixture was warmed to 40° for 3 hrs. The mixture was poured into 1000 ml of ice-water, containing 65 g of ammonium chloride. The mixture was heated on a steam bath for 2 hrs and extracted with ether. The ether extract was washed with saturated sodium bicarbonate, dried over anhydrous magnesium sulfate and the solvent was removed in vacuo to yield an oil. The oil was purified by high pressure liquid chromatography (7% methanol in acetone) to yield the desired ketone (9.00 g, 17%) as an oil. The oil was dissolved in ether and a dilute solution of oxalic acid/ether was added. The salt was collected, washed with ether and recrystallized two times from ethyl acetate to yield product as the oxalate, mp, 160°–162°.

ANALYSIS: Calculated for $C_{13}H_{15}F_2NO \cdot HO_2C-CO_2H$: 54.68%C, 4.86%H, 4.25%N. Found: 55.06%C, 5.12%H, 4.60%N.

EXAMPLE 15

4-(2,4-Difluorobenzoyl)-1-formylpiperidine oxime

A solution of 12 g of ammonium acetate in 45 ml of water was added to a solution of 15 g of 4-(2,4-difluorobenzoyl)-1-formylpiperidine and 6 g of hydroxylamine hydrochloride in 35 ml of ethanol. The mixture was heated for 18 at 90°, with stirring. The solution was evaporated in vacuum until precipitation occurred. Water (500 ml) was added. The mixture was filtered, washed with 300 ml of water and dried in vacuum over phosphorous pentoxide to yield 12 g (75.5%) of product. Recrystallization from ethanol and water yielded the analytical sample, mp, 185°.

ANALYSIS: Calculated for $C_{13}H_{14}F_2N_2O_2$: 58.18%C, 5.26%H, 10.44%N. Found: 58.40%C, 4.99%H, 10.43%N.

EXAMPLE 16

1-Acetyl-4-(2-hydroxy-5-methoxybenzoyl)piperidine oxime

A solution of 15.5 g of 1-acetyl-4-(2-hydroxy-5-methoxybenzoyl)piperidine, 7.0 g of hydroxylamine hydrochloride, 9.5 g of ammonium acetate and 75 ml of water was heated under reflux for 20 hrs. The solution was poured into water and extracted with dichloromethane. The dichloromethane extract was washed with water, dried over anhydrous magnesium sulfate and the solvent was removed in vacuo to give an oil. The oil was triturated with hot toluene. The toluene was decanted and the oil was triturated with ether to give a solid. The tolulene triturant, upon standing, yielded a solid. The solids were combined and recrystallized from acetonitrile to yield 2.8 g (17.4%) of product, mp, 191°–193°, as a mixture of E- and Z-isomers. The chromatogram showed 2 spots.

ANALYSIS: Calculated for $C_{15}H_{20}N_2O_4$: 61.65%C, 6.90%H, 9.59%N. Found: 61.44%C, 6.76%H, 9.57%N.

EXAMPLE 17

1-Acetyl-4-(4,5-dimethoxy-2-hydroxy)piperidine oxime

A mixture of 14.0 g of 1-acetyl-4-(2-hydroxy-4,5-dimethoxyl)piperidine, 5.6 g of hydroxylamine hydrochloride, 7.6 g of ammonium acetate, 225 ml of ethanol and 70 ml of ether was stirred and heated under reflux for 18 hrs. Most of the ether was removed under pressure to leave a biphasic mixture. The mixture was diluted with water and extracted with dichloromethane. The organic extract was dried over anhydrous magnesium sulfate and the solvent was removed under pressure to yield 22.1 g of product as an oily mixture of E- and Z-isomers. A 14.0 g sample of the oil was chromatographed on a Waters model 500 Preparative High Pressure Liquid Chromatograph. Using (dichloromethane/methanol (4.0%) as the eluent, 3.5 g of starting material, 2.9 g (20.7%) of the less polar oxime (E-isomer) and 5.6 g (39.9%) of the more polar oxime (Z-isomer) were obtained. The less polar oxime (E-isomer) was recrystallized from ethyl acetate to give product as a solid, mp 151°–153°. Although the chromatographed oxime was essentially one isomer, upon recrystallization, the compound isomerized, which resulted in a mixture of E- and Z-isomers.

ANALYSIS: Calculated for $C_{16}H_{22}N_2O_5$: 59.61%C, 6.88%H, 8.69%N. Found: 59.33%C, 6.76%H, 8.65%N.

EXAMPLE 18

1-Acetyl-4-(5-fluoro-2-hydroxybenzoyl)piperidine oxime

A mixture of 12.7 g of 1-acetyl-4-(5-fluoro-2-hydroxybenzoyl)piperidine, 6.6 g of hydroxylamine hydrochloride, 11.0 g of ammonium acetate and 200 ml of ethanol-ether was heated under reflux for 10 hrs. After cooling, most of the ethanol was removed under reduced pressure. The resultant suspension was diluted with water and extracted with dichloromethane. The dichloromethane was evaporated in vacuo to given an oil. The oil was dissolved in ethyl acetate and cyclohexane was added to precipitate a solid. The solid was recrystallized from ethyl acetate to give 8.8 g (65.4%) of product, mp, 181°–183°. The chromatogram showed 2 spots.

ANALYSIS: Calculated for $C_{14}H_{17}FN_2O_3$: 59.99%C, 6.12%H, 10.00%N. Found: 59.82%C, 6.11%H, 9.89%N.

EXAMPLE 19

Z,1-Acetyl-4-(5-fluoro-2-hydroxybenzoyl)piperidine O-acetyloxime

A mixture of 197 g of 1-acetyl-4-(5-fluoro-2-hydroxybenzoyl)piperidine oxime, 195 ml of acetic anhydride and 400 ml dichloromethane was stirred at ambient temperature for 16 hrs. A solid precipitated. The solid was collected to give 127 g of product, predominantly as the Z isomer, mp, 195°–197°. The dichloromethane filtrate was washed with water, aqueous sodium bicarbonate solution, dried over anhydrous magnesium sulfate and the solvent removed in vacuo to give a solid. The solid was triturated with either and collected to yield 47.8 g of product, predominantly the E isomer. Total yield was 174.8 g (77.5%). A 4.0 g sample of the Z-rich fraction was recrystallized from dimethylformamide to give 2.9 g of Z-isomer, mp, 206°–208°.

ANALYSIS: Calculated for $C_{16}H_{18}FN_2O_4$: 59.65%C, 5.94%H, 8.69%N. Found: 59.64%C, 6.03%H, 8.74%N.

EXAMPLE 20

1-Acetyl-4-(2,4-dichlorobenzoyl)piperidine oxime

A mixture of 13.0 g of 4-(2,4-dichlorobenzoyl)-N-acetylpiperidine, 6.8 g of hydroxylamine hydrochloride, 13.5 g of ammonium acetate, 127 ml of ethanol and 43 ml of water was stirred and heated at 130° for 24 hrs. The reaction mixture was evaporated and 1.3 l of water was added to the residue. The water was decanted from the oil and the oil was dissolved in about 150 ml dichloromethane. After washing with about 150 ml of water, drying over anhydrous magnesium sulfate and evaporating the solvent, an oil was obtained, which after crystallization from methanol/ether gave 4.25 g (31.1%) of product, mp, 167°–168°.

ANALYSIS: Calculated for $C_{14}H_{16}Cl_2N_2O_2$: 53.36%C, 5.12%H, 8.89%N, 22.50% Cl. Found: 53.25%C, 5.14%H, 8.82%N, 22.22%Cl.

EXAMPLE 21

1-Formyl-4-(2,4-dichlorobenzoyl)piperidine oxime a. To a stirred slurry of 125 g of aluminum chloride in 735 g of 1,3-dichlorobenzene, was added 97 g of 1-formylisonipecotyl chloride. The mixture was heated to ca 70° and then at ca 120° for 2.5 hrs, with stirring. The unreacted dichlorobenzene was distilled in vacuum at 70° (16 mm). The residue was decomposed with 4 l of ice-water and 50 ml of conc hydrochloric acid. After 17 hrs, the oil was separated by decantation. The oil was washed twice with about 2 l of water and dissolved in 1 l of dichloromethane. The dichloromethane extract was washed with 500 ml of 2N sodium hydroxide, two times with 500 ml of water and dried over anhydrous magnesium sulfate. The dichloromethane was distilled to yield 110 g (64%) of product as an oil.

b. A mixture of 105 g of 4-(2,4-dichlorobenzoyl)-1-formylpiperidine, 70 g of hydroxylamine hydrochloride, 135.0 g of ammonium acetate, 1.05 l of ethanol and 350 ml of water was stirred and heated at 130° for 40 hrs. The reaction mixture was evaporated and 2 l of water was added to the residue. The water was decanted from the oil and oil was washed two times with 500 ml water and then dissolved in about 400 ml dichloromethane. The insoluble material was collected. The dichloromethane extract was washed twice with 600 ml of water and the organic extract was evaporated. Trituration with diisopropyl ether and crystallization from acetone/ether gave 15.6 g (14.2%) of product, mp, 149°–150°.

ANALYSIS: Calculated for $C_{13}H_{14}Cl_2N_2O_2$: 51.86% C, 4.86%H, 9.29%N. Found: 51.94%C, 4.86%H, 9/08%N.

EXAMPLE 22

4-(2,4-Dichlorobenzoyl)piperidine oxime hydrochloride

A mixture of 105 g of 4-(2,4-dichlorobenzoyl)-1-formylpiperidine, 70 g of hydroxylamine hydrochloride, 135 g of ammonium acetate, 1.05 l of ethanol and 350 ml of water was stirred and heated at 130° for 40 hrs. The reaction mixture was evaporated and 2.0 l of water was added to the residue. The water was decanted from the oil and the oil was washed two times with 500 ml of water and dissolved in about 400 ml of dichloromethane. The insoluble material was collected. The dichloromethane extract was washed twice with 600 ml of water. The combined aqueous phases were made basic with potassium carbonate/water. The precipitate was filtered, washed with water and dried over phosphorus pentoxide in vacuo to yield 27.2 g (9.96%) of 4-(2,4-dichlorobenzoyl)piperidine oxime. The insoluble material was dissolved in hot water and made alkaline with potassium carbonate-water. The precipitate was filtered, washed with water and dried over phosphorus pentoxide in vacuo. The solid was dissolved in 200 ml methanol and 2 ml of conc hydrochloric acid was added. After heating for 5 mins, the solution was filtered and evaporated in vacuo to dryness. The residue was recrystallized from methanol-ether to yield product as the hydrochloride, mp 284°.

ANALYSIS: Calculated for $C_{12}H_{15}C_{12}N_2O$ HCl: 46.53%C, 4.88%H, 9.05%N. Found: 46.75%C, 5.00%H, 8.97%N.

EXAMPLE 23

Z,4-(2-hydroxy-4-methoxybenzoyl)-1-piperidine carboxylic acid phenylmethyl ester oxime A solution of 39.0 g of 4-(2-hydroxy-3-methoxybenzoyl)-1-piperidine carboxylic acid phenylmethyl ester, 10.9 g of hydroxylamine hydrochloride, 18.2 g of ammonium acetate, 600 ml/180 ml of ethanol/water was heated under reflux for 24 hrs. Most of the ethanol was removed in vacuo to yield a biphasic mixture. The mixture was extracted with dichloromethane. The dichloromethane extract was washed with water, dried over anhydrous magnesium sulfate and the solvent was removed in vacuo to given an oil. The oil was dissolved in either and a solid precipitated from solution. The solid was collected to give 19.9 g (49.3%) of product. The solid corresponded to one of the isomers. Removal of the filtrate gave an oil, which was rich in the other isomer. A 3.0 g sample of the solid was recrystallized from ethyl acetate-hexane to yield 2.8 g of product as the Z-isomer, mp, 155°–156°.

ANALYSIS: Calculated for $C_{21}H_{24}N_2O_5$: 65.60%C, 6.24%H, 7.29%N. Found: 65.58%C, 6.26%H, 7.42%N.

EXAMPLE 24

1-Methyl-4-(2-fluorobenzoyl)piperidine oxime

A mixture of 5.2 g of 1-methyl-4-(2-fluorobenzoyl)-piperidine, 2.5 g of hydroxylamine hydrochloride, 5.4 g of ammonium acetate and 50+15 ml of ethanol-water was heated under reflux for 22 hrs. Most of the ethanol was removed under reduced pressure. The aqueous mixture was made basic with aqueous sodium hydroxide and the mixture was extracted with chloroform. The chloroform extract was dried over anhydrous magnesium sulfate and the chloroform was evaporated in vacuo to give a solid. The solid was triturated with ether. Recrystallization from ethanol-water gave 3.0 g (52.6%) of product, mp, 136°–139°.

ANALYSIS: Calculated for $C_{13}H_{17}N_2O$: 66.08%C, 7.25%H, 11.86%N. Found: 65.80%C, 7.21%H, 11.86%N.

EXAMPLE 25

4-(2,4-Difluorobenzoyl)-1-allylpiperidine oxime hydrochloride

A suspension of 4.80 g of 4-(2,4-difluorobenzoyl)-piperidine oxime, 2.7 g of allyl bromide, 2.7 g of ammonium chloride and some crystals of potassium iodide in 50 ml of dimethylformamide was stirred under nitrogen at 85°–90° for 5 hrs. The reaction mixture was cooled, diluted with 30 ml of ethanol and added to 1000 ml of half saturated aqueous sodium chloride solution, prepared by diluting saturated sodium chloride solution with an equal volume of water. After 16 hrs, the solid was washed with water and dried. The solid was dissolved in 60 ml of ethanol and 1 ml of conc hydrochloric acid. After heating to 50°, the solvents were evaporated in vacuo. Recrystallization of the residue from isopropanol-ether gave 2.63 g (43.5%) of product, mp, 239°.

ANALYSIS: Calculated for $C_{15}H_{18}F_2N_2O_1$ HCl: 56.89%C, 6.04%H, 8.84%N. Found: 56.66%C, 5.90%H, 8.74%N.

EXAMPLE 26

3-(1-Methyl-4-piperidyl)-5-methyl-1,2-benzisoxazole fumarate

A solution of 50 g of 1-methyl-4-(2-chloro-5-methylbenzoyl)piperidine, 32 g of hydroxylamine hydrochloride, 120 g of 85% potassium hydroxide, 700 ml of ethoxyethanol and 700 ml of water was heated under reflux for 10 hrs and then stirred at room temperature for 6 hrs. The reaction mixture was poured into 5 l of water and extracted with petroleum ether three times. The extracts were washed with sodium chloride solution and dried over anhydrous sodium sulfate. The solvent was removed under reduced pressure to give 11 g (24%) of product as an oil. The fumarate salt was made by dissolving 4.5 g of the benzisoxazole in 20 ml of acetonitrile, containing 2.25 g of fumaric acid, and stirring for 2 hrs. The precipitate was filtered and recrystallized three times from ethanol-ether to give analytical product, mp, 179.5°–180.5°.

ANALYSIS: Calculated for $C_{14}H_{18}N_2O$ $C_4H_4O_4$: 62.41%C, 6.40%H, 8.09%N. Found: 62.23%C, 6.34%H, 8.08%N.

EXAMPLE 27

4-Fluoro-3-(1-methyl-4-piperidyl)-1,2-benzisoxazole hydrochloride

A stirred mixture of 209 g of 1-methyl-4-(2,6-difluorobenzoyl)piperidine, 400 g of potassium hydroxide, 102 g of hydroxylamine hydrochloride, 2100 ml of isopropanol and 2100 ml of water was refluxed for 10 hrs and then stirred overnight at ambient temperature. The reaction mixture was poured into water and extracted with hexane. The hexane extracts were dried over anhydrous magnesium sulfate, filtered and the solvent was removed in vacuo to yield a solid. The solid was purified by passing it through a silica gel column (15:1) using 1% methanol in dichloromethane as eluent. Evaporation of the eluent provided a solid, which was dissolved in ether. A hydrochloric acid-ether solution was added dropwise. The precipitate was collected and washed with ether to yield 24.71 g (14%) of product, mp, 221°–223°.

ANALYSIS: Calculated for $C_{13}H_{15}FN_2O$ HCl: 57.90%C, 5.57%H, 10.39%N. Found: 57.79%C, 5.97%H, 10.13%N.

EXAMPLE 28

6-Methoxy-3-(1-acetyl-4-piperidyl)-1,2-benzisoxazole a. A stirred mixture of 10.0 g of 1-acetyl-4-(2-hydroxy-4-methoxybenzoyl)piperidine and 10 ml of acetic anhydride was heated to 60° for 10 mins and cooled to ambient temperature to yield an oil. Hexane was added to the oil. The hexane was decanted and the oil was poured into water and extracted with ethyl acetate. The ethyl acetate layer was washed with saturated sodium bicarbonate solution, dried over anhydrous magnesium sulfate and the solvent was removed in vacuo to yield 7.50 g of 1-acetyl-4-(2-hydroxy-4-methoxybenzoyl)piperidine o-acetyl oxime as an oil.

b. In a 3-neck round-bottom flask equipped with a mechanical stirrer and dropping funnel was added 1.20 g of a 50% sodium hydride oil dispersion. The sodium hydride was washed two times with anhydrous ethyl ether and the supernate was removed with a pipette. A solution of 7.50 g of 1-acetyl-4-(2-hydroxy-4-methoxybenzoyl)piperidine o-acetyl oxime in 45 ml of dimethylformamide was added dropwise while the reaction mixture was stirred vigorously. The solution was stirred for 18 hrs at ambient temperature and poured into water. The mixture was extracted with ethyl acetate, dried over anhydrous magnesium sulfate and the solvent was removed in vacuo to yield an oil, which was triturated with petroleum ether to yield 3.0 g of a solid. The solid was combined with 1.64 g of previously prepared material and recrystallized 2 times from isopropyl ether to yield 2.80 g (29.5%) of product, mp, 91°–93°.

ANALYSIS: Calculated for $C_{15}H_{18}O_3N_2$: 65.62%C, 6.56%H, 10.21%N. Found: 65.93%C, 6.63%H, 10.05%N.

EXAMPLE 29

4-(6-Methoxy-1,2-benzisoxazol-3-yl)-1-piperidine carboxylic acid phenylmethyl ester a. A solution of 13.3 g of 4-(2-hydroxy-4-methoxybenzoyl)-1-piperidine carboxylic acid phenylmethyl ester oxime (mostly of the E-configuration) and 3.6 ml of acetic anhydride in 70 ml of dichloromethane was stirred at ambient temperature for 16 hrs. Evaporation of the dichloromethane gave E, 4-(2-hydroxy-4-methoxybenzoyl-3-yl)-1-piperidine carboxylic acid phenylmethyl ester oxime acetate as an oil.

b. The acetate (16.4 g) was stirred and refluxed with 7.9 g of potassium carbonate and 30 ml of methanol for 2 hrs. The reaction mixture was poured into water and the aqueous suspension extracted with ethyl acetate. The ethyl acetate extract was washed with brine, dried over anhydrous magnesium sulfate and the ethyl acetate removed in vacuo to yield 13.2 g of an oil. The oil (8.7 g) was chromatographed on a Waters Prep 500 using two silica gel golumns eluting with dichloromethane-methanol (1%). Two batches were isolated as solids, one containing the pure compound and the other slightly contaiminated with a more polar material. The former batch was recrystallized from isopropyl ether and, after concentration of the mother liquor, yielded 2.1 g (38%) of product, mp 66°–68°.

ANALYSIS: Calculated for $C_{21}H_{22}N_2O_4$: 68.83%C, 6.05%H, 7.64%N. Found: 68.83%C, 5.98%H, 7.63%N.

EXAMPLE 30

5-Methoxy-3-(1-acetyl-4-piperidyl)-1,2-benzisoxazole a. A mixture of 10.0 g of E,1-acetyl-4-(2-hydroxy-5-methoxybenzoyl)piperidine E oxime and 4.5 ml of acetic anhydride was heated at 60° for 1.5 hrs. The resultant solid was stirred with ether and collected to yield 7.0 g of the E,1-acetyl-4-(2-hydroxy-5-methoxybenzoyl)piperidine oxime acetate.

b. The 1-acetyl-4-(2-hydroxy-5-methoxybenzolyl)-piperidine oxime acetate (7.0 g) was added slowly to a stirred suspension of 1.1 g of ether-washed sodium hydride (50% oil dispersion) in 80 ml of dimethylformamide. The reaction was stirred at ambient temperature for 16 hrs and then poured into 300 ml of water. The aqueous solution was extracted 3×with 150 ml of ethyl acetate. The extracts were combined, washed with brine and water and dried over anhydrous magnesium sulfate. Evaporation of the ethyl acetate under reduced pressure yielded an oil. The oil crystallized upon trituration with ether to a solid. The solid was recrystallized from toluene-cyclohexane and then from isopropyl ether to give 2.1 g (36.5%) of product, mp, 103°–105°.

ANALYSIS: Calculated for $C_{15}H_{18}N_2O_3$: 65.67%C, 6.61%H, 10.21%N. Found: 65.76%C, 6.59%H, 10.31%N.

EXAMPLE 31

5,6-Dimethoxy-3-(1-acetyl-4-piperidyl-1,2-benzisoxazole

To a round-bottom flask equipped with a condenser was added 3.47 g of 1-acetyl-4-(2-hydroxy-4,5-dimethoxybenzoyl)piperidine oxime acetate (predominately the E-isomer), 1.60 g of potassium carbonate and 30 ml of methanol. The mixture was stirred under reflux for 3.0 hrs and overnight at ambient temperature. The reaction mixture was poured into water. The solid was collected, washed well with water and recrystallized from ethyl acetate to yeild 2.00 g (68.5%) of product, mp, 195°–197°.

ANALYSIS: Calculated for $C_{16}H_{20}N_2O_4$: 63.12%C, 6.57%H, 9.21%N. Found: 62.79%C, 6.66%H, 8.92%N.

EXAMPLE 32

3-(1-Acetyl-4-piperidyl)-5-fluoro-1,2-benzisoxazole

A 7.6 g sample of sodium hydride (50% oil dispersion) was washed with hexane and then suspended in 500 ml of dimethylformamide. The suspension was then stirred virorously under nitrogen and 47.8 g of 1-acetyl-4-(5-fluoro-2-hydroxybenzoyl)piperidine o-acetyl oxime (mostly E-isomer) was added slowly. The reaction was stirred at ambient temperature for 16 hrs and then poured into water. A solid separated from solution. The solid was filtered and dried to give 21.6 g of the product, mp, 158°–160°. The filtrate was extracted with ethyl acetate. The extract was washed with water, dried over anhydrous magnesium sulfate and evaporated. The residue was recrystallized from isopropyl alcohol-water and from toluene-hexane to give an additional 2.9 g of product, mp 158°–160°. Total yield was 63%.

ANALYSIS: Calculated for $C_{14}H_{15}F_2N_2O_2$: 64.11%C, 5.76%H, 10.68%N. Found: 64.18%C, 5.80%H, 10.58%N.

EXAMPLE 33

3-(1-Formyl-4-piperidyl)-6-chloro-1,2-benzisoxazole a. To the mixed anhydride, prepared by dropping 40 ml of formic acid (98%), over 15 mins, into 80 ml of aceticanhydride at 20° (ice cooling necessary), removing the ice-bath, allowing the temperature of the mixture to warm to 55°–60° and, after 30 mins the mixture cooled to 15°, was added, over 5 mins, with stirring and cooling in an ice-bath, 15.0 g of 4-(2,4-dichlorobenzoyl)-piperidine oxime. After stirring in an ice bath for 6 hrs and stirring at 20° for 16 hrs, the mixed anhydride was distilled in vacuum using an oil bath (80°). The residue was washed twice with 400 ml of water, dissolved in 200 ml of dichloromethane, and after washing with 300 ml of water, the solvent was distilled in vacuo. Upon standing, the residue crystallized, yielding 15 g (90%) of 1-formyl-4-(2,4-dichlorobenzoyl)piperidine oxime formate. A sample recrystallized from dissopropylether-ether had, mp, 117°–177°.

b. To a stirred suspension of 1.25 g of sodium hydride (prepared from 2.5 g 50% oil dispersion) in 100 ml of tetrahydrofuran was added, over 20 mins, a solution of 10 g of 1-formyl-4-(2,4-dichlorobenzoyl)piperidine O-formyl oxime in 60 ml of dimethylformamide and 40 ml of tetrahydrofuran. The stirred mixture was heated to 80°–90° (oil bath temperature) for 5 hrs and after standing at 20° for 16 hrs, 10 ml of methanol and 20 ml of water were added. The reaction mixture was added to about 1.2 l of saturated sodium chloride solution. The mixture was extracted with 400 ml of ether. The extract was washed with 800 ml of water. The aqueous phase was extracted with 400 ml of ether and the combined ether extracts were distilled to yield an oil, which crystallized on standing. Recrystallization from isopropanol-ether gave 6.5 g (67.2%) of product, mp 114°–115°.

ANALYSIS: Calculated for $C_{13}H_{13}ClN_2O_2$: 58.98%C, 4.95%H, 10.59%N. Found: 58.71%C, 4.89%H, 10.47%N.

EXAMPLE 34

3-(1-Methyl-4-piperidyl)-1,2-benzisoxazole hydrochloride

To a solution of 28.2 g of 1-methyl-4-(2-fluorobenzoyl)piperidine and 19.2 g of hydroxylamine in 400 ml of monethooxyethanol and 200 ml of water, was added 80.8 g of 85% potassium hydroxide dissolved in 200 ml of water. The solution was heated under reflux under nitrogen for 5 hrs., cooled, poured into 1.5 l of water and the aqueous solution was extracted with 3×400 ml of ether. The ether extracts were combined, washed with water, dried over anhydrous potassium carbonate and the solvent removed in vacuo to give an oil. The oil was dissolved in ether and hydrogen chloride was added. The salt was dissolved in water, treated with aqueous sodium hydroxide solution and extracted with petroleum ether (b.p. 30°–69°). The petroleum ether extract was dried over anhydrous potassium carbonate and the petroleum ether evaporated to give 16.9 of an oil. Treatment of the oil with hydrogen chloride in ether and subsequent recrystallization from ethanol-ether gave 15.4 g (47%) of product, mp 250°–252°.

ANALYSIS: Calculated for $C_{13}H_{16}N_2O$ HCl: 61.77%C, 6.38%H, 11.08%N. Found: 61.59%C, 6.66%H, 10.93%N.

EXAMPLE 35

3-(4-Piperidyl)-6-fluoro-1,2-benzisoxazole hydrochloride

A solution of 3.8 g of 3-(1-formyl-4-piperidyl)-6-fluoro-1,2-benzisoxazole was dissolved in 45 ml of ethanol (96%) and 45 ml of 3N hydrochloric acid was heated under reflux for 3 hrs. The mixture was diluted with water to 500 ml, made alkaline with potassium carbonate solution and extracted with dichloromethane (5×200 ml). The combined extracts were washed with water, dried over anhydrous magnesium sulfate and the dichloromethane was removed in vacuo to give 3.7 g of an oil. The oil was dissolved in 30 ml of methanol and 1 ml of concentrated hydrochloric acid was added. The methanol was distilled, 15 ml benzene was added and also distilled. The residue was treated with 100 ml of ether to give a solid. Two recrystallizations from isopropanol-methanol-ether yielded 1.25 g (31.8%) of product, mp, 293°–295°.

ANALYSIS: Calculated for $C_{12}H_{13}FN_2O$ HCl: 56.15%C, 5.49%H, 10.91%N. Found: 56.99%C, 5.66%H, 10.51%N.

EXAMPLE 36

5-Methoxy-3-(4-piperidyl)-1,2-benzisoxazole hydrochloride

A mixture of 7.6 g of 1-acetyl-5-methoxy-3-(4-piperidyl)-1,2-benzisoxazole and 45 ml of 6N hydrochloric acid was heated under reflux for 6 hrs. On standing for 8 hrs, the solution deposited a solid which was filtered and dried to yield 3.2 g of product as the hydrochloride salt. The aqueous filtrate was made basic with 50% sodium hydroxide and the basic solution was extracted with ether. The ether was removed in vacuo and the oil was converted with ether-hydrogen chloride to give 1.1 g of product as the hydrochloride salt. The combined salts were recrystallized three times from methanol-ether to yield 1.7 g (23%) of product hydrochloride, mp, 274°–277°.

ANALYSIS: Calculated for $C_{13}H_{16}N_2O_2$ HCl: 58.09%C, 6.38%H, 10.43%N. Found: 58.27%C, 6.49%H, 10.50%N.

EXAMPLE 37

5,6-Dimethoxy-3-(4-piperidyl)-1,2-benzisoxazole hydrobromide

A solution of 13.0 g of 5,6-dimethoxy-3-(1-acetyl-4-piperidyl)-1,2-benzisoxazole and 80 ml of 6N hydrochloric acid was stirred under reflux for 6 hrs and overnight at ambient temperature. The mixture was poured into water, basified with 10% sodium hydroxide and extracted with ethylacetate. The extract were dried over anhydrous magnesium sulfate and the solvent was removed in vacuo to yield a solid. The solid was dissolved in a minimum amount of ethanol-ether and the product as the hydrobromide salt was precipitated with a saturated hydrogen bromide-ether solution. The salt was recrystallized from ethanol-ether to yield 4.50 g of product hydrobromide, mp, 235°–237°.

ANALYSIS: Calculated for $C_{14}H_{18}N_2O_3$ HBr: 48.99%C, 5.25%H, 8.17%N. Found: 48.86%C, 5.48%H, 7.98%N.

EXAMPLE 38

5-Fluoro-3-(4-piperidyl)-1,2-benzisoxazole hydrochloride

A mixture of 17.5 g of 3-(1-acetyl-4-piperidyl)-5-fluoro-1,2-benzisoxazole and 110 ml of 6N hydrochloric acid was stirred under reflux for 6 hrs. After standing at ambient temperature for ca 12 hrs, a solid was collected, washed with acetone and dried to yield 14.2 g (83%) of product as the hydrochloride salt, mp 297°–299°.

ANALYSIS: Calculated for $C_{12}H_{13}FN_2O$ HCl: 56.14%C, 5.50%H, 10.92%N. Found: 56.15%C, 5.41%H, 10.84%N.

EXAMPLE 39

6-Methoxy-3-(4-piperidyl)-1,2-benzisoxazole hydrobromide

To 30 ml of a saturated solution of hydrogen bromide and acetic acid was added, with stirring, 0.88 g of 4-(6-methoxy-1,2-benzisoxazol-3-yl)-1-piperidine carboxylic acid phenylmethyl ester. The reaction was stirred at ambient temperature for 55 min. The resultant solid was collected, washed with ether and dried to yield 0.5 g (79.8%) of product. Recrystallization from methanol gave the analytical sample, mp 258°–260°.

ANALYSIS: Calculated for $C_{13}H_{16}N_2O_2$ HBr: 49.85%C, 5.47%H, 8.95%N. Found: 49.94%C, 5.41%H, 8.84%N.

EXAMPLE 40

3-(4-Piperidyl)-6-chloro-1,2-benzisoxazole hydrochloride

A solution of 19 g of 3-(1-formyl-4-piperidyl)-6-chloro-1,2-benzisoxazole in 225 ml of ethanol (96%) and 225 ml of 3N hydrochloric acid was heated under reflux for 3 hrs. After 30 mins, the ethanol and the water were distilled in vacuo. Benzene (100 ml) was added and distilled. Recrystallization from isopropanol-ether yielded 16.4 of salt. A 4 g sample was recrystallized from ethanol-ether to give 3.55 g (74.2%) of product as the hydrochloride, mp, 228°–229°.

ANALYSIS: Calculated for $C_{12}H_{13}ClN_2O$ HCl: 52.75%C, 5.16%H, 10.25%N. Found: 52.59%C, 5.13%H, 10.17%N.

EXAMPLE 41

4-(4-Fluoro-1,2-benzisoxazol-3-yl)-1-piperidine carboxylic acid phenyl ester A mixture of 1.74 g of 4-fluoro-3-(1-methyl-4-piperidyl)-1,2-benzisoxazole, 1.25 g of potassium carbonate, 1.40 g of phenyl chloroformate and 50.0 ml of toluene was stirred under reflux for 8.0 hrs. The mixture was poured into water and the toluene layer was separated, dried over anhydrous magnesium sulfate and the solvent was removed in vacuo to yield an oil. The oil was purified by passing through a silica gel column (20:1), using 1% methanol in dichloromethane as the eluent. The eluent was evaporated and the residue solidified when scratched to yield a solid. The solid was recrystallized from petroleum-ether (bp 30°–60°) to yield 1.6 g (64%) of product, mp 108°–110°.

ANALYSIS: Calculated for $C_{19}H_{17}FN_2O_3$: 67.06%C, 5.00%H, 8.24%N. Found: 67.03%C, 5.20%H, 8.12%N.

EXAMPLE 42

5-Hydroxy-3-(4-piperidyl)-1,2-benzisoxazole hydrobromide

A mixture of 5.4 g of 1-acetyl-5-methoxy-3-(4-piperidyl-1,2-benzisoxazole and 48% hydrogen bromide was heated under reflux for 10 hrs and the precipitate was collected. Recrystallization from methanol-ether afforded 3.0 g (50.9%) of product hydrobromide, mp, 293°–295°.

ANALYSIS: Calculated for $C_{12}H_{14}N_2O_2$ HBr: 48.17%C, 5.05%H, 9.37%N. Found: 48.12%C, 5.00%H, 9.47%N.

EXAMPLE 43

4-(1,2benzisoxazol-3-yl)-1-piperidine carboxylic acid phenyl ester

A mixture of 12.3 g of 3-(1-methyl-4-piperidyl)-1,2-benzisoxazole hydrochloride and aqueous sodium hydroxide was extracted into 200 ml of toluene. The toluene solution was dried over anhydrous magnesium sulfate, filtered and 8.8 g of phenyl chloroformate was added. The mixture was was heated under reflux under nitrogen for 16 hrs and cooled. The toluene was removed under reduced pressure and the resultant oil was taken up in ether. Petroleum ether (bp 30°–60°) was added and the precipitate was collected to give 12.3 g (78%) of product, mp, 96°–98°. Recrystallization of a sample from ethanol-water gave the analytical sample, mp, 107°–109°.

ANALYSIS: Calculated for $C_{19}H_{18}N_2O_3$: 70.79%C, 5.63%H, 8.69%N. Found: 71.11%C, 5.69%H, 8.84%N.

EXAMPLE 44

3-(4-Piperidyl)-1,2-benzisoxazole hydrochloride

A mixture of 5.0 g of 4-(1,2-benzisoxazole-3-yl)-1-piperidine carboxylic acid phenyl ester, 100 ml of ethanol, 50 g of (85%) potassium hydroxide and 50 ml of water was heated under reflux, with stirring, under nitrogen for 16 hrs. Most of the ethanol was removed in vacuo and the resultant aqueous suspension was extracted with ether (3×50 ml). The ether extracts were combined, washed with water, dried over anhydrous magnesium sulfate and the ether removed under reduced pressure to give an oil. The oil was dissolved in anhydrous ether and hydrogen chloride was introduced to precipitate a 3.0 g of a hydrochloride salt. Recrystallization from methanol-ether gave 2.0 g (57%) of product as the hydrochloride, mp, 313°–315° (dec.).

ANALYSIS: Calculated for $C_{12}H_{14}N_2O$ HCl: 60.37%C, 6.33%H, 11.74%N. Found: 60.52%C, 6.32%H, 11.67%N.

EXAMPLE 45

3-[1-(3-Dimethylaminopropyl)-4-piperidyl]-1,2-benzisoxazole difumarate

A suspension of 3.5 g of 3-(4-piperidyl)-1,2-benzisoxazole, 2.3 g of 3-dimethylaminopropyl chloride, 5.0 g of sodium bicarbonate and 3.0 g of potassium iodide in 100 ml of n-butanol was heated under reflux for 2 hrs, cooled to room temperature and filtered. The filtrate was washed with water and extracted with ether (3 times). The ether extract was dried over anhydrous sodium sulfate and the solvent was removed under reduced pressure to give 3.9 g of oil. The oil was dissolved in 15 ml of acetonitrile and 1.6 g of fumaric acid was added. The precipitate was filtered and recrystallized from methanol to give 2.2 (25%) of product, mp, 196°–197°.

ANALYSIS: Calculated for $C_{17}H_{25}N_3O$ $2C_4H_4O_4$: 57.80%C, 6.48%H, 8.09%N. Found: 57.73%C, 6.43%H, 7.98%N.

EXAMPLE 46

3-[1-(3-Diethylaminopropyl)-4-piperidyl]-1,2-benzisoxazole difumarate

A suspension of 4.0 g of 3-(4-piperidyl)-1,2-benzisoxazole, 3.2 g of 3-diethylaminopropyl chloride, 3.0 g of potassium iodide and 5.0 g of sodium bicarbonate in 100 ml of butanol was heated under reflux for 2 hrs, cooled to room temperature and filtered. The filitrate was washed with water and extracted with ether (3 times). The ether extracts were dried over anhydrous sodium sulfate, filtered and evaporated to give an oil. The oil was dissolved in 10 ml of acetonitrile and 4.2 g of fumaric acid was added. The mixture was stirred for 2 hrs, filtered and the filter cake was recrystallized three times from ethanol-ether to give 2.8 g (26%) of product, mp 174°–176°.

ANALYSIS: Calculated for $C_{19}H_{29}N_3O$ $2C_4H_4O_4$: 59.22%C, 6.81%H, 7.67%N. Found: 59.26%C, 7.01%H, 7.33%N.

EXAMPLE 47

3-[1-(2-Dimethylaminoethyl)-4-piperidyl]-1,2-benzisoxazole difumarate

A suspension of 4.5 g of 3-(4-piperidyl)-1,2-benzisoxazole, 2.6 g of 2-dimethylaminoethyl chloride, 3.0 g of potassium iodide and 5.0 g of potassium carbonate in 100 ml of butanol was heated under reflux for 2 hrs, cooled to room temperature and filtered. The filtrate was washed with water and extracted with ether (3 times). The ether extracts were dried over anhydrous sodium sulfate and the solvent was removed under reduced pressure to give an oil. The oil was dissolved in 10 ml of acetonitrile and 3.2 g of fumaric acid was added. The reaction mixture was stirred for 2 hrs, filtered and the filter cake was recrystallized three times from ethanol-ether to give 2.2 g (19.8%) of product, mp, 215°–217°.

ANALYSIS: Calculated for $C_{19}H_{29}N_3O$ $2C_4H_4O_4$: 57.02%C, 6.18%H, 8.31%N. Found: 57.41%C, 6.21%H, 8.20%N.

EXAMPLE 48

3-[1-(2-Diethylaminoethyl)-4-piperidiyl]-1,2-benzisoxazole difumarate

A suspension of 4.0 g of 3-(4-piperidyl)-1,2-benzisoxazole, 2.9 g of 2-diethylaminoethyl chloride, 5.0 g of sodium bicarbonate and 3.0 g of potassium iodide in 100 ml of n-butanol was heated under reflux for 2 hrs, cooled to room temperature and filtered. The butanol was removed under reduced pressure and the residue was dissolved in ether, washed with water and saturated sodium chloride, dried over anhydrous sodium sulfate and the solvent was removed to give 3.0 g of an oil. The oil was dissolved in 10 ml of acetonitrile and 2.2 g of fumaric acid was added. The suspension was stirred for 2 hrs. The precipitate was filtered and recrystallized from ethanol-ether (4 times) to give 2.9 g (28.6%) of product, mp, 192°–193.5°.

ANALYSIS: Calculated for $C_{18}H_{27}N_3O$ $2C_4H_4O_4$: 58.53%C, 6.61%H, 7.88%N. Found: 58.44%C, 6.68%H, 7.95%N.

EXAMPLE 49

3-(1-Allyl-4-piperidyl)-6-fluoro-1,2-benzisoxazole hydrochloride

A suspension of 4.95 g of 3-(4-piperidyl)-6-fluoro-1,2-benzisoxazole, 3.0 g of allyl bromide, 3.0 g of potassium carbonate and some crystals of potassium iodide in 70 ml of dimethylformamide was stirred under nitrogen at 85°–90° for 5 hrs. The reaction was cooled and added to 40 ml ethanol. Half-saturated sodium chloride, prepared by adding an equal volume of water to saturated sodium chloride solution was added. After 16 hrs, the crystals were filtered, washed with water and dried, yielding 3.4 g of base. The base was dissolved in 60 ml of ethanol and 1.5 ml conc hydrochloric acid. The mixture was heated to 50° and the solvents were evaporated in vacuo. Benzene (60 ml) was added and distilled off in vacuo, yielding a residue. The residue was triturated with ether, filtered and twice recrystallized from isopropanol-ether to give 2.4 g (59.3%) of product, mp, 198°.

ANALYSIS: Calculated for $C_{15}H_{18}FClN_2O$: 60.69%C, 6.11%H, 9.43%N. Found: 60.36%C, 6.15%H, 9.21%N.

EXAMPLE 50

3-(1-Allyl-4-piperidyl)-6-chloro-1,2-benzisoxazole hydrochloride

A suspension of 3.55 g of 3-(4-piperidyl)-6-chloro-1,2-benzisoxazole, 2.0 g of allyl bromide, 2.0 g of potassium carbonate and some crystals of potassium iodide in 47 ml of dimethylformamide was stirred under nitrogen at 85°–90° for 5 hrs. The reaction mixture was cooled and filtered. The crystals were washed with dichloromethane. The combined organic solvents (dimethylformamide + dichloromethane) were distilled in vacuo and to the residue was added with 30 ml ethanol and 500 ml half-saturated sodium chloride, prepared by diluting saturated sodium chloride with an equal volume of water. After 16 hrs, the crystals were filtered, washed with water and dried, yielding base. The base was dissolved in 50 ml of ethanol and 1.2 ml of conc hydrochloric acid. The mixture was heated to 50°. The solvents were evaporated in vacuo. Benzene (60 ml) was added and distilled in vacuo. The residue was triturated with ether, filtered and twice recrystallized from isopropanol-ether, giving 3.0 g (63.9%) of product as the hydrochloride, mp, 178°–180°.

ANALYSIS: Calculated for $C_{15}H_{17}ClN_2O$: 57.54%C, 5.79%H, 8.94%N. Found: 57.43%C, 5.69%H, 8.92%N.

EXAMPLE 51

3-(1-Allyl-4-piperidyl)-1,2-benzisoxazole hydrochloride

A suspension of 4.0 g of 3-(4-piperidyl)-1,2-benzisoxazole, 2.6 g of allyl bromide, 5.0 g of sodium bicarbonate, and 3.0 g of potassium iodide in 90 ml of dimethylformamide was stirred at 80° for 20 hrs. The reaction was cooled, filtered and poured into 1 l of water. The mixture was extracted with ether (three times) and dried over anhydrous sodium sulfate. The solvent was removed under reduced pressure to give an oil. The oil was dissolved in a small amount of ether into which hydrochloric acid was bubbled. The precipitate was recrystallized from ethanol-ether (three times) to give 2.4 g of product, mp, 174°–176°.

ANALYSIS: Calculated for $C_{15}H_{18}N_2O$ HCl: 64.62%C, 6.87%H, 10.05%N. Found: 64.61%C, 6.87%H, 9.88%N.

EXAMPLE 52

3-(1-Cyclopropylmethyl-4-piperidyl)-1,2-benzisoxazole hydrochloride

To a suspension of 5.0 g of 3-(4-piperidyl)-1,2-benzisoxazole, 5.5 g of sodium bicarbonate and 3.0 g of potassium iodide in 75 ml of dimethylformamide was added, dropwise, 2.4 g of cyclopropylmethyl chloride in 25 ml of dimethylformamide, with stirring. The reaction was stirred at 80° for 20 hrs, cooled to room temperature and filtered. The filtrate was poured into 1 l of water and extracted with ether (three times). The ether extracts were washed with saturated sodium bicarbonate solution, saturated sodium chloride solution and dried over anhydrous sodium sulfate. The solvent was removed to give an oil, which was dissolved in ether into which sodium chloride was bubbled. The precipitate was collected and recrystallized twice from ethanol to give 3.5 g of product, mp, 234.5°–236°.

ANALYSIS: Calculated for $C_{16}H_{20}N_2O$ HCl: 65.36%C, 7.23%H, 9.57%N. Found: 65.68%C, 7.30%H, 9.56%N.

EXAMPLE 53

3-[1-(β-Phenylethyl)-4-piperidyl]-1,2-benzisoxazole hydrochloride

To a suspension of 5.0 g of 3-(4-piperidyl)-1,2-benzisoxazole, 5.5 g of sodium bicarbonate and 3.0 g of potassium iodide in 75 ml of dimethylformamide at 60° was added dropwise 5.0 g of β-phenylethyl bromide in 15 ml of dimethylformamide, with stirring. The reaction was stirred at 60° for 20 hrs, cooled to room temperature and filtered. The filtrate was poured into 1 l of water and allowed to stand overnight. The solid was filtered, dried and dissolved in ether into which hydrochloric acid was bubbled. The precipitate was recrystallized twice from ethanol to give 4.1 g (48%) of product, mp, 216°–217°.

ANALYSIS: Calculated for $C_{20}H_{22}N_2O$ HCl: 70.06%C, 6.76%H, 8.17%N. Found: 70.01%C, 6.55%H, 8.22%N.

EXAMPLE 54

3-(1-Benzoyloxy-4-piperidyl)-1,2-benzisoxazole

A suspension of 5.0 g of 3-(4-piperidyl)-1,2-benzisoxazole, 6 g of benzoyl peroxide and 6.8 g of potassium carbonate in 100 ml of benzene was stirred at room temperature for 18 hrs. The reaction was filtered and the solvent was removed under reduced pressure to give 7.5 g (97%) of product. A small amount was recrystallized once from acetone and three times from ethanol to give the analytical sample, mp, 156°–158°.

ANALYSIS: Calculated for $C_{19}H_{18}N_2O_3$: 70.79%C, 5.63%H, 8.69%N. Found: 70.68%C, 5.62%H, 8.66%N.

EXAMPLE 55

3-(1-Hydroxy-4-piperidyl)-1,2-benzisoxazole hydrochloride

A solution of 4.1 g of 3-(1-benzoyloxy-4-piperidyl)-1,2-benzisoxazole, 55 ml of ethanol and 35 ml of 10% sodium hydroxide solution was heated under reflux for 45 mins, cooled to room temperature and the ethanol removed under reduced pressure. The residue was added to 50 ml of water and the pH of the solution was adjusted to 6 with careful addition of 6N hydrochloric acid. The solution was extracted with chloroform. The chloroform extracts were dried over anhydrous sodium sulfate and the solvent was removed under reduced pressure. The residue was dissolved in ether and a solution of ether-hydrochloric acid was added. The precipitate was collected and recrystallized from ethanol-ether (three times) to give 2.1 g (63%) of product, mp 213°–216°.

ANALYSIS: Calculated for $C_{12}H_{14}N_2O_2$ HCl: 56.85%C, 5.94%H, 11.00%N. Found: 56.59%C, 6.01%H, 11.16%N.

EXAMPLE 56

6-Fluoro-3-(1-cyanomethyl-4-piperidyl)-1,2-benzisoxazole

A mixture of 3.1 g of 6-fluoro-3-(4-piperidyl)-1,2-benzisoxazole hydrochloride, 4.9 g of potassium carbonate and 30 ml of dimethylformamide was stirred at ambient temperature for 5 min. Potassium iodide (0.24 g) was added, followed by 0.76 ml of chloroacetonitrile. The mixture was stirred and heated under nitrogen at 80°–85° for 2 hrs and then poured into 300 ml of water. The solid was collected and dried (vacuum oven). Recrystallization from ethanol-water yielded 2.0 g (64%) of product. An analytical sample was obtained by combining the 2.0 g sample with 0.8 g of another sample and recrystallizing from ethanol-water to give 2.2 g of product, mp, 126°–128°.

ANALYSIS: Calculated for $C_{14}H_{14}FN_3O$: 64.85%C 5.44%H 16.21%N Found: 64.86%C 5.45%H 16.07%N

EXAMPLE 57

3-(1-Cyano-4-piperidyl)-5-methyl-1,2-benzisoxazole

A suspension of 0.5 g of 3-(1-methyl-4-piperidyl)-5-methyl-1,2-benzisoxazole, 0.37 g of cyanogen bromide and 1.5 g of potassium carbonate in 50 ml of chloroform was heated under reflux for 48 hrs and stirred at room temperature for 48 hrs. The reaction was filtered, the solvent was removed and the residue was triturated with hexane to give a solid. The solid was recrystallized from hexnae (three times) to give 0.178 g (37%) of product, mp, 125°–126°.

ANALYSIS: Calculated for $C_{14}H_{15}N_3O$: 69.69%C, 6.27%H, 17.41%N. Found: 69.43%C, 6.19%H, 17.76%N.

EXAMPLE 58

3-(1-Cyano-4-piperidyl)-1,2-benzisoxazole

A suspension of 4.8 g of 3-(4-piperidyl)-1,2-benzisoxazole, 2.7 g of cyanogen bromide, 5.0 g of sodium bicarbonate and 3.0 g of potassium iodide in 100 ml of chloroform was heated under reflux overnight. The reaction was cooled to room temperature, filtered and concentrated in vacuo to give a solid. The benzisoxazole was purified on 120 g of silica gel, eluted with chloroform and recrystallized twice from acetone-hexane to give 3.4 g (62.3%) of product, mp, 115°–117°.

ANALYSIS: Calculated for $C_{13}H_{13}N_3O$: 68.70%C, 5.77%H, 18.49%N. Found: 68.58%C, 5.90%H, 18.38%N.

EXAMPLE 59

4-(2-Fluorobenzoyl)-1-methylpiperidine hydrochloride

To a suspension of 7.6 g of magnesium turnings in 25 ml of tetrahydrofuran was added a few drops of ethyl bromide, with stirring under nitrogen. After the reaction began, approximately 50.0 g of N-methyl-4-chloropiperidine in 125 ml of tetrahydrofuran was added dropwise at a rate such as to maintain moderate reflux. The reaction mixture was heated under reflux an additional hr, and 37.2 g of 2-fluorobenzonitrile in 50 ml of tetrahydrofuran was added dropwise. After completion of the addition, the reaction mixture was refluxed for two hrs, and stirred overnight at room temperature. The reaction mixture was poured into a solution of 85 g of ammonium chloride in 1200 ml of ice water and heated on a steam bath for 3 hrs. The mixture was cooled, extracted with benzene (3×250 ml), dried over anhydrous sodium sulfate, and the excess solvent was removed under reduced pressure to give 62.72 g (91%) of 4-(2-fluorobenzoyl)-1-methyl piperidine as an oil. A small amount of 4-(2-fluorobenzoyl)-1-methyl piperidine (1.0 g) was removed, dissolved in ether and a solution of ethereal hydrochloric acid was added. The precipitate was collected, dried and recrystallized from ethanol-ether (2×) to give 0.5 g of 4-(2-fluorobenzoyl)-1-methylpiperidine hydrochloride, mp, 167°–169°.

ANALYSIS: Calculated for $C_{13}H_{17}ClFNO$: 60.58%C, 6.65%H, 5.43%N, 7.37%F. Found: 60.30%C, 6.78%H, 5.43%N, 7.59%F.

EXAMPLE 60

3-(1-Formyl-4-piperidyl)-6-fluoro-1,2-benzisoxazol

To a stirring suspension of 1.34 g of sodium hydride (50% oil dispersion washed two times with hexane and the hexane decanted) in 40 ml of tetrahydrofuran/dimethylformamide (3:1) was added, dropwise, 7.0 g of 1-formyl-4-(2,4-difluorobenzoyl)piperidine oxime in 40 ml of tetrahydrofuran/dimethylformamide (3:1). The mixture was then stirred at 90° for 3 hrs. Sodium hydride (0.77 g of 50% oil-dispersion treated as above) was added. The mixture was stirred an additional hour at 90°. The heater was removed. The following day the mixture was heated at 90° for 5 hrs. An additional 0.5 g of sodium hydride (50% oil-dispersion treated as above) was added. Heating and stirring were continued for 5 hrs. The reaction mixture was cooled, poured into water, and the aqueous suspension extracted with ether. (3 times, 250 ml). The ether extracts were combined, washed with brine and water and then dried over anhydrous magnesium sulfate. Evaporation of the solvent gave an oil, which was triturated with ether to give a solid. The filtrate was concentrated to an oil, which crystallized to a solid upon standing. The solid was triturated with ether to give 1.0 g (15.4%) of product.

We claim:
1. 4-(4-Fluoro-1,2-benzisoxazol-3-yl)-1-methyl-1-phenoxycarbonylpiperidinium chloride.
2. 4-(5-Methyl-1,2-benzisoxazol-3-yl)-1-cyano-1-methylpiperidinium bromide.

* * * * *

UNITED STATES PATENT AND TRADEMARK OFFICE
CERTIFICATE OF CORRECTION

PATENT NO. : 4,469,869

DATED : September 4, 1984

INVENTOR(S) : Joseph T. Strupczewski; Beth A. Gardner; Richard C. Allen

It is certified that error appears in the above-identified patent and that said Letters Patent is hereby corrected as shown below:

Column 2, Line 60

" loweralkyl halogen " should be -- loweralkyl, halogen --

Column 6, Line 16

" cyllization " should be -- cyclization --

Column 15 & 16   Reaction Scheme E

" HO    N     HO    N "   should be   -- HO~N     HO~N   "

Column 17 & 18   Reaction Scheme G

" UCN    "   should be   --  UCN    ---
   14                         41

Column 23, LIne 37

" 18 at 90° "   should be   --  18 hours at 90°  --

Column 24, Line 40

" given " should be -- give --

Column 24, Line 64

" either " should be -- ether --

Column 26, Line 34

" given " should be -- give --

Column 26, Line 35

" either " should be -- ether --

Column 28, Line 51

" golumns eluting " should be -- columns and eluting --

Column 25, Line 56

" 9/08%N " should be -- 9.08%N

UNITED STATES PATENT AND TRADEMARK OFFICE
CERTIFICATE OF CORRECTION

PATENT NO. : 4,469,869

DATED : September 4, 1984

INVENTOR(S) : Joseph T. Strupczewski; Beth A. Gardner; Richard C. Allen

It is certified that error appears in the above-identified patent and that said Letters Patent is hereby corrected as shown below:

Column 34, Line 26

" wasdissolved " should be -- was dissolved --

Signed and Sealed this

Sixteenth Day of July 1985

[SEAL]

Attest:

DONALD J. QUIGG

Attesting Officer     Acting Commissioner of Patents and Trademarks